(12) United States Patent
Foster et al.

(10) Patent No.: US 12,162,781 B2
(45) Date of Patent: Dec. 10, 2024

(54) SINGLE ENDED, ANTI-VIBRATION IMPROVED LAMP DESIGN

(71) Applicant: ATG UV TECHNOLOGY LTD, Lancashire (GB)

(72) Inventors: George Foster, Whitefield (GB); Richard Joshi, Lowton (GB)

(73) Assignee: ATG R&D Limited, Wigan (GB)

( * ) Notice: Subject to any disclaimer, the term of this patent is extended or adjusted under 35 U.S.C. 154(b) by 360 days.

(21) Appl. No.: 17/632,231

(22) PCT Filed: Jul. 31, 2020

(86) PCT No.: PCT/GB2020/051852
§ 371 (c)(1),
(2) Date: Feb. 1, 2022

(87) PCT Pub. No.: WO2021/019256
PCT Pub. Date: Feb. 4, 2021

(65) Prior Publication Data
US 2022/0267174 A1      Aug. 25, 2022

Related U.S. Application Data

(60) Provisional application No. 62/881,673, filed on Aug. 1, 2019.

(51) Int. Cl.
*C02F 1/32* (2023.01)
*A61L 2/10* (2006.01)
*C02F 1/72* (2023.01)

(52) U.S. Cl.
CPC ............. *C02F 1/325* (2013.01); *A61L 2/10* (2013.01); *C02F 1/72* (2013.01); *C02F 2201/3223* (2013.01); *C02F 2201/3228* (2013.01); *C02F 2201/326* (2013.01); *C02F 2303/04* (2013.01)

(58) Field of Classification Search
CPC ..... B01J 19/12; C02F 1/32; C02F 1/36; C02F 1/30; C02F 1/46; H01J 61/34; H01J 61/52
See application file for complete search history.

(56) References Cited

U.S. PATENT DOCUMENTS 5,505,912 A * 4/1996 Hallett .................. B01J 19/123
422/906

FOREIGN PATENT DOCUMENTS

WO    WO-2014029632 A2 * 2/2014 ............. C02F 1/325

OTHER PUBLICATIONS

International Search Report in corresponding PCT/GB2020/051852, dated Oct. 7, 2020.

* cited by examiner

*Primary Examiner* — Walter D. Griffin
*Assistant Examiner* — Cameron J Allen
(74) *Attorney, Agent, or Firm* — ATG R&D Limited

(57) ABSTRACT

A water treatment system includes an actinic radiation reactor and at least one ultraviolet (UV) lamp disposed within a quartz tube within the actinic radiation reactor. The at least one UV lamp includes a lamp tube including a gas that emits ultraviolet light responsive to electrical excitation, a first pinch extending from a first end of the lamp tube and a second pinch extending from a second end of the lamp tube, and a first end cap coupled to the first pinch and a second end cap coupled to the second pinch. The first end cap and second end cap are dimensioned to center the lamp tube coaxially within the quartz tube.

21 Claims, 21 Drawing Sheets

SINGLE ENDED, ANTI-VIBRATION IMPROVED LAMP DESIGN

BACKGROUND

1. Field of Invention

Aspects and embodiments disclosed herein are generally directed to ultraviolet lamps, and in some specific embodiments, to ultraviolet lamps suitable for use in advanced oxidation systems and to methods of operating or constructing same.

2. Discussion of Related Art

Ultraviolet (UV) apparatus are used extensively in water purification applications. UV can be used to disinfect water by destroying harmful bacteria is such applications as drinking water and aquatics. When UV is used for disinfection, the typical wavelength employed is 254 nm. UV can also be used to generate free radicals which can be used to destroy organic compounds in aqueous solutions. When used to destroy organic compounds, a wavelength of 185 nm is typically used.

A UV apparatus normally comprises a housing, a quartz tube and a UV lamp that fits inside the quartz tube. The quartz tube separates the liquid to be treated from the UV lamp. The UV lamp has electrical connections that are connected to a power supply. As a liquid is passed through the housing, it is irradiated by UV light to photochemically destroy bacteria and/or organic compounds.

SUMMARY

In accordance with an aspect of the present disclosure, there is provided a water treatment system. The water treatment system comprises an actinic radiation reactor and at least one ultraviolet (UV) lamp disposed within a quartz tube within the actinic radiation reactor. The at least one UV lamp includes a lamp tube including a gas that emits ultraviolet light responsive to electrical excitation, a first pinch extending from a first end of the lamp tube and a second pinch extending from a second end of the lamp tube, and a first end cap coupled to the first pinch and a second end cap coupled to the second pinch. The first end cap and second end cap are dimensioned to center the lamp tube coaxially within the quartz tube.

In some embodiments, the UV lamp further includes thermally conductive biasing elements disposed about respective peripheries of each of the first end cap and second end cap. The thermally conductive biasing elements may comprise metallic springs. The thermally conductive biasing elements may be disposed within grooves defined within and circumscribing outer peripheral surfaces of the first end cap and the second end cap.

In some embodiments, portions of the outer peripheral surfaces of the first end cap and second end cap are contoured to conform to an inner surface of the quartz tube.

In some embodiments, the first and second end caps include slots extending inwardly from the outer peripheral surfaces. The slots may be perpendicular to the grooves.

In some embodiments, the system further comprises an electrical conductor configured to provide power to the lamp tube disposed within the slots. The metallic springs may retain the conductor within the slots.

In some embodiments, the thermally conductive biasing elements contact an inner surface of the quartz tube, support the lamp tube within the quartz tube, and dampen vibrations passing from the quartz tube to the first and second end caps.

In some embodiments, in operation, the lamp tube exhibits a symmetric temperature profile from the first pinch to the second pinch.

In some embodiments, the actinic radiation reactor is an ultraviolet advanced oxidation process reactor.

In accordance with another aspect, there is provided a method of treating water. The method comprises introducing the water into an inlet of an actinic radiation reactor including at least one ultraviolet (UV) lamp disposed within a quartz tube within the actinic radiation reactor. The at least one UV lamp includes a lamp tube including a gas that emits ultraviolet light responsive to electrical excitation, a first pinch extending from a first end of the lamp tube and a second pinch extending from a second end of the lamp tube, and a first end cap coupled to the first pinch and a second end cap coupled to the second pinch, the first end cap and second end cap dimensioned to center the lamp tube coaxially within the quartz tube. The method further includes irradiating the water within the actinic radiation reactor with UV light from the at least one UV lamp to produce treated water and withdrawing the treated water from the actinic radiation reactor.

In accordance with another aspect, there is provided an ultraviolet (UV) lamp configured to be disposed within a quartz tube within an actinic radiation reactor. The UV lamp comprises a lamp tube including a gas that emits ultraviolet light responsive to electrical excitation, a first pinch extending from a first end of the lamp tube and a second pinch extending from a second end of the lamp tube, a first end cap coupled to the first pinch and a second end cap coupled to the second pinch, the first end cap and second end cap dimensioned to center the lamp tube coaxially within the quartz tube, and a means for vibrationally isolating at least one of the first end cap and the second end cap from the quartz tube disposed about respective peripheries of each of the first end cap and second end cap.

In some embodiments, the means for vibration dampening comprises a thermally conductive element.

In some embodiments, the thermally conductive elements comprise metallic springs.

In some embodiments, the metallic springs are disposed within grooves defined within and circumscribing outer peripheral surfaces of the first end cap and the second end cap.

In some embodiments, portions of the outer peripheral surfaces of the first end cap and second end cap are contoured to conform to an inner surface of the quartz tube.

In some embodiments, the first and second end caps include slots extending inwardly from the outer peripheral surfaces.

In some embodiments, the slots are perpendicular to the grooves.

In some embodiments, the UV lamp further comprises an electrical conductor configured to provide power to the lamp tube disposed within the slots.

In some embodiments, the metallic springs retain the electrical conductor within the slots.

In some embodiments, the thermally conductive elements contact an inner surface of the quartz tube, support the lamp tube within the quartz tube, and dampen vibrations passing from the quartz tube to the first and second end caps.

In some embodiments, in operation, the lamp tube exhibits a symmetric temperature profile from the first pinch to the second pinch.

In accordance with another aspect, there is provided a method of retrofitting an actinic radiation reactor. The method comprises replacing at least one ultraviolet (UV) lamp within the actinic radiation reactor with a replacement lamp. The replacement lamp includes a lamp tube including a gas that emits ultraviolet light responsive to electrical excitation, a first pinch extending from a first end of the lamp tube and a second pinch extending from a second end of the lamp tube, and a first end cap coupled to the first pinch and a second end cap coupled to the second pinch, the first end cap and second end cap dimensioned to center the lamp tube coaxially within a quartz tube in the actinic radiation reactor.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
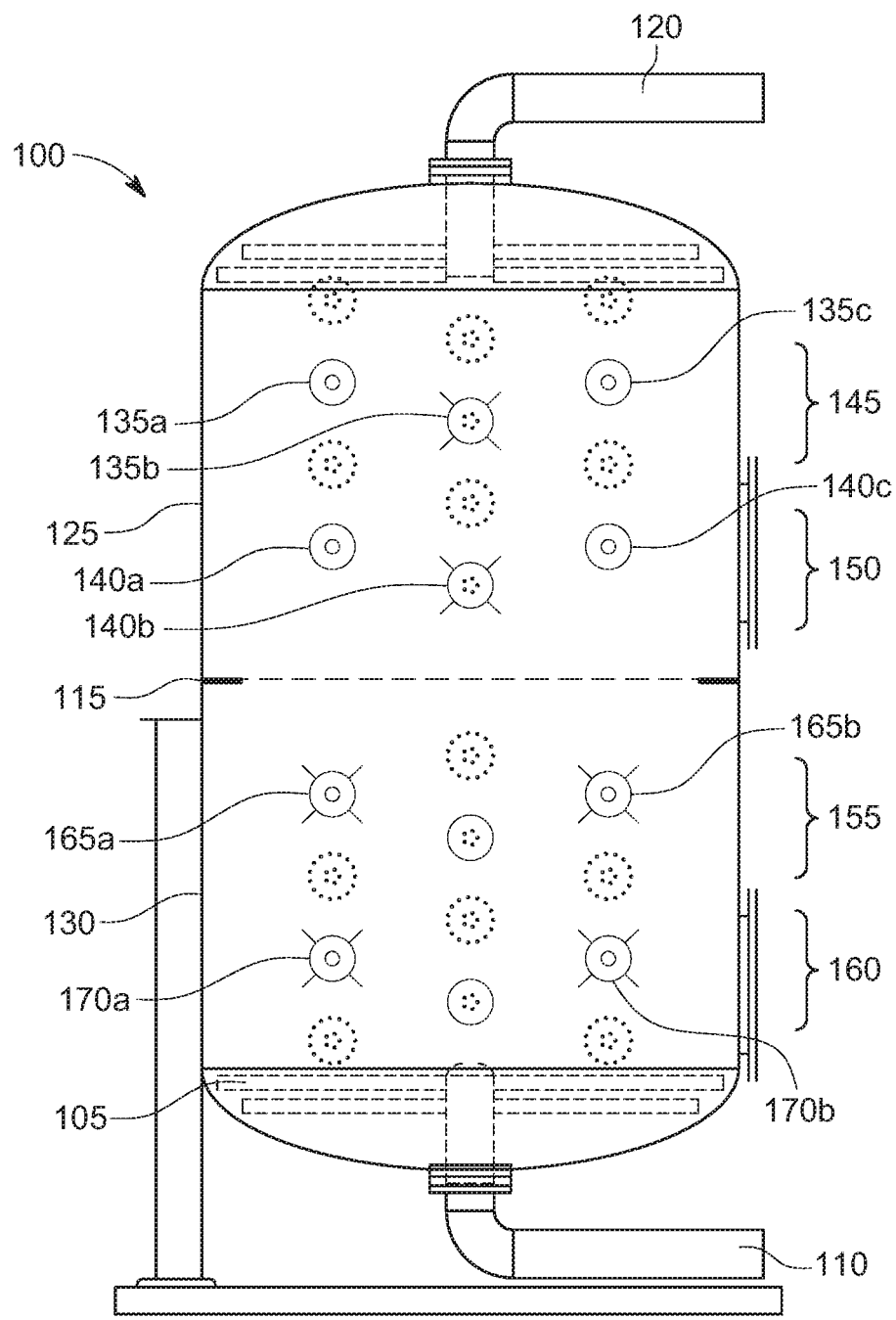
FIG. 1 is a schematic drawing illustrating an actinic radiation reactor vessel in in accordance with one or more embodiments.

Aspects and embodiments disclosed herein are not limited to the details of construction and the arrangement of components set forth in the following description or illustrated in the drawings. Aspects and embodiments disclosed herein are capable of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Aspects and embodiments disclosed herein relate generally to ultra-violet (UV) lamp systems and improvements designed to extend the life and prevent premature failure of the UV lamp systems.

Conventional UV lamp systems are problematic due to an unacceptably high risk of electrical shock, burn, and exposure to UV-C radiation inherent in the design of such systems. Removal of a UV lamp while energized exposes the operator to UV light radiation, extreme heat, and potential electrical shock.

Conventional solutions to the problem do not completely eliminate the inherent risks. One such system utilizes a large electrical enclosure with an access port. This system does not completely mitigate the risks because the access port could be carelessly left open. Another system utilizes a mechanical trip switch to de-energize the lamp upon removal. This system also fails to completely mitigate the risks because the switch can fail.

Aspects and embodiments of UV lamps or UV lamp systems disclosed herein may include one or more features that increase the reliability and lifetime of the UV lamps or UV lamp systems as compared to previously known UV lamps or UV lamp systems. In some embodiments heat flow from a UV lamp into an external environment may be improved (increased) as compared to previously known UV lamps. Operating temperatures of embodiments of UV lamps disclosed herein may be lower and/or more uniform and symmetric across the lamps than in previously known UV lamps. Embodiments of UV lamps disclosed herein may be more resistant to damage due to vibration than previously known UV lamps.

Aspects and embodiments disclosed herein may be directed to systems for treating contaminated wastewater. Aspects and embodiments disclosed herein may be directed to systems that utilize ultraviolet radiation treatment to reduce the total organic carbon (TOC) content of water to be treated. Aspects and embodiments disclosed herein may be directed to systems for purifying water to a degree that it is suitable for use as drinking water, irrigation water, or as deionized water in labs or in semiconductor manufacturing plants. Water to be treated in aspects and embodiments of systems disclosed herein may be any one or more of industrial or municipal wastewater, groundwater, or return water from lab wash operations or semiconductor manufacturing operations.

One or more aspects disclosed herein relate to a system for treating contaminated wastewater. In some embodiments, the system comprises a source of contaminated wastewater having an initial concentration of a recalcitrant organic contaminant, a TOC concentration sensor in fluid communication with the contaminated wastewater, a source of a precursor for one or more free radical species fluidly connected to the source of contaminated wastewater and configured to introduce the precursor into the contaminated wastewater, a UV reactor including UV lamps as disclosed herein fluidly connected to the source of contaminated wastewater and configured to irradiate the contaminated wastewater, and a controller in communication with the TOC concentration sensor and configured to control at least one of a rate at which the precursor is introduced to the contaminated wastewater and a dose of irradiation applied by the UV lamps based on an output signal from the TOC concentration sensor. The precursor may be or may include, for example, hydrogen peroxide or a persulfate species.

According to another aspect, the controller is configured to control the dose of irradiation by controlling a residence time of the contaminated wastewater in the reactor. According to yet another aspect, the controller is configured to control the dose of irradiation by controlling a flow rate of the contaminated wastewater.

According to a further aspect, the UV reactor is positioned downstream from the source of precursor. According to at least one aspect, the TOC concentration sensor is positioned upstream from the source of precursor. According to another aspect, the TOC concentration sensor is a first TOC concentration sensor and the system further comprises a second TOC concentration sensor in communication with the controller and positioned downstream from the UV reactor. According to certain aspects, the controller is configured to control at least one of the rate at which the precursor is introduced into the contaminated wastewater and a dose of irradiation applied by the UV lamps based on an output signal from the second TOC concentration sensor.

One or more aspects can be directed to wastewater treatment systems and techniques. The systems and techniques may utilize a precursor for one or more free radicals in combination with a source of ultraviolet (UV) light to treat wastewater contaminated with a recalcitrant organic contaminant. According to some embodiments, the wastewater is treated such that the concentration of recalcitrant organic contaminant is reduced to levels such that the wastewater may be pumped back into the ground, i.e., the level of recalcitrant organic contaminant falls below one or more standards set by governing authorities. According to a further aspect, the concentration of recalcitrant organic contaminant is reduced such that the treated wastewater may be characterized as potable water. For example, according to some embodiments, the methods and systems disclosed herein may treat contaminated wastewater to produce potable water. The potable water may comply with standards set by municipalities. As used herein the term "recalcitrant organic" when used in reference to a contaminant refers to organic compounds that resist microbial degradation or are not readily biodegradable. In certain instances, the recalcitrant organic contaminant may not degrade biologically, and remediation methods may be unable to remove enough of the substance to satisfy environmental regulations. Non-limiting examples of recalcitrant organic contaminants include 1,4-dioxane, trichloroethylene (TCE), perchloroethylene (PCE), urea, isopropanol, chloroform, atrazine, tryptophan, and formic acid.

In accordance with at least one aspect, some embodiments involve a method for treating contaminated wastewater. In addition, the process may be used to remediate contaminated groundwater. As used herein, the term "groundwater" may refer to water recoverable from subterranean sources as well as water recovered from surface bodies of water, such as streams, ponds, marshes, and other similar bodies of water. The wastewater or groundwater may be contaminated with a recalcitrant organic contaminant, as discussed above. The wastewater may have become contaminated from any one of a number of different sources, such as industrial processes, agricultural process, such as pesticide and herbicide applications, or other processes, such as disinfection processes that produce undesirable byproducts such as trihalomethanes.

In accordance with at least one embodiment, the methods and systems disclosed herein may include providing a contaminated wastewater having an initial concentration of a recalcitrant organic contaminant. According to some embodiments, the methods and systems disclosed herein may include extracting or otherwise removing the contaminated wastewater. For instance, the contaminated wastewater may be pumped from the ground or other sources using one or more pumps or other extraction devices as part of a remediation effort. Once treated, the wastewater may then be discharged or sent on for further processing. According to some embodiments, the contaminated wastewater is pumped or otherwise removed to the surface grade level where it may then be treated according to the processes and methods discussed herein. For example, according to some embodiments, the methods and systems disclosed herein may include extracting the contaminated wastewater from a remediation site. In at least one embodiment, one or more extraction wells and extraction equipment, such as pumps, may be used for pumping contaminated wastewater to the surface to be treated. Once treated, a pump or other distribution system may be used to re-inject the treated wastewater or groundwater back into the ground or otherwise re-introduce the treated wastewater back into the environment. In certain instances the contaminated wastewater may be stored in a holding tank or vessel prior to treatment, and in some cases treated water produced by the processes disclosed herein may be added or otherwise mixed with the contaminated wastewater.

In accordance with one or more aspects, the contaminated wastewater may have a level of total dissolved solids (TDS) that is in a range of about 100 mg/L to about 5000 mg/L, and in some instances may be in a range of about 200 mg/L to about 2000 mg/L, although these values can vary depending on the geographic location and other factors. As a source of comparison, water with a TDS level of 1000-1500 mg/L is considered drinkable, with some standards having a 500 mg/L TDS limit for domestic water supplies.

In accordance with another aspect, the methods and systems disclosed herein may be connected or otherwise in fluid communication with a source of contaminated wastewater. For instance, the contaminated wastewater may be pumped or otherwise delivered to the disclosed system for treatment.

According to various aspects, the concentration of recalcitrant organic contaminant in the wastewater is high enough to exceed limits established by government agencies. According to some embodiments, the systems and methods disclosed herein treat the wastewater such that the concentration level of the recalcitrant organic contaminant is reduced. In some instances, the systems and methods disclosed herein reduce the concentration of the recalcitrant organic contaminant to a level that complies with government standards or guidelines. According to one embodiment, the concentration of recalcitrant organic contaminant is reduced to a level such that the treated wastewater may be reintroduced back into the environment. For example, the EPA's standard for the concentration of 1,4-dixoane in drinking water is 1 µg/L (1 ppb). The methods and systems disclosed herein may be scaled to treat substantially all concentrations of recalcitrant organic contaminant that may be present in the wastewater. For instance, according to some embodiments, the initial concentration of recalcitrant organic contaminant, such as dioxane, in the wastewater may be in a range from about 5 ppb to about 800 ppb.

Advanced oxidation processes (AOP) are a set of treatment procedures used to remove organic materials from wastewater. In many applications, these processes involve the use of UV light and hydrogen peroxide, specifically:

(homolytic bond cleavage of the O—O bond of $H_2O_2$ leads to formation of 2.OH radicals)

Systems disclosed herein may include an actinic radiation reactor, for example, a UV reactor, that receives one or more oxidants (e.g., $H_2O_2$, ammonium persulfate, potassium persulfate, or other persulfate species) to facilitate destruction, e.g., oxidation, of one or more contaminants in water undergoing treatment in the actinic radiation reactor. The actinic radiation reactor can comprise a vessel, and a first array of tubes in the vessel. The first array of tubes can comprise a first set of parallel tubes, and a second set of parallel tubes. Each tube can comprise at least one ultraviolet lamp and each of the parallel tubes of the first set is positioned to have its longitudinal axis orthogonal relative to the longitudinal axis of the tubes of the second set.

In examples of an actinic radiation reactor utilized in systems disclosed herein, organic compounds in water undergoing treatment can be oxidized by one or more free radical species into carbon dioxide, which can be removed in one or more downstream unit operations. The actinic radiation reactor can comprise at least one free radical activation device that converts one or more precursor compounds into one or more free radical scavenging species, for example, the hydroxyl radical $OH^-$ or the sulfate radical $SO_4^{2-}$. The actinic radiation reactor can comprise one or more lamps, in one or more reaction chambers, to irradiate or otherwise provide actinic radiation to the water and divide the precursor compound into the one or more free radical species.

The reactor can be divided into two chambers by one or more baffles between the chambers. The baffle can be used to provide mixing or turbulence to the reactor or prevent mixing or promote laminar, parallel flow paths through the interior of the reactor, such as in the chambers. In certain embodiments, a reactor inlet is in fluid communication with a first chamber and a reactor outlet is in fluid communication with a second chamber.

In some embodiments, at least three reactor chambers, each having at least one ultraviolet (UV) lamp disposed to irradiate the water in the respective chambers with light of about 185 nm, 220 nm, and/or 254 nm, or ranging from about 185 nm to about 254 nm, at various power levels, are serially arranged in reactor. It is to be appreciated that the shorter wavelengths of 185 nm or 220 nm may be preferable in AOP processes because UV light at these wavelengths has sufficient photon energy to create free radicals from free radical precursors utilized in the process for oxidizing dissolved organic contaminants. In contrast, disinfection processes, where UV light may be utilized to kill or disable microorganisms, may operate efficiently with UV light at the 254 nm wavelength produced by low pressure lamps. Disinfection systems would not typically utilize the more expensive medium pressure or high pressure UV lamps capable of providing significant UV intensity at the shorter 185 nm or 220 nm wavelengths.

The one or more lamps can be positioned within the one or more actinic radiation reactors by being placed within one or more sleeves or tubes within the reactor. The tubes can hold the lamps in place and protect the lamps from the water within the reactor. The tubes can be made of any material that is not substantially degraded by the actinic radiation and the water or components of the water within the reactor, while allowing the radiation to pass through the material. The tubes can have a cross-sectional area that is circular. In certain embodiments, the tubes can be cylindrical, and the material of construction thereof can be quartz. Each of the tubes can be the same or different shape or size as one or more other tubes. The tubes can be arranged within the reactor in various configurations, for example, the sleeves may extend across a portion of or the entire length or width of the reactor. The tubes can also extend across an inner volume of the reactor.

Commercially available quartz sleeves may be obtained from Enterprise Q (Manchester, UK), Multi-Lab (Newcastle Upon Tyne, UK), or Glass Automated Products, Inc. (Huntington Beach, Calif.). The quartz material selected can be based at least in part on the particular wavelength or wavelengths that will be used in the process. The quartz material may be selected to minimize the energy requirements of the ultraviolet lamps at one or more wavelengths. The composition of the quartz can be selected to provide a desired or suitable transmittance of ultraviolet light to the water in the reactor and/or to maintain a desired or adequate level of transmissivity of ultraviolet light to the water. In certain embodiments, the transmissivity can be at least about 50% for a predetermined period of time. For example, the transmissivity can be about 80% or greater for a predetermined period of time. In certain embodiments, the transmissivity can be in a range of about 80% to 90% for about 6 months to about one year. In certain embodiments, the transmissivity can be in a range of about 80% to 90% for up to about two years.

The tubes can be sealed at each end so as to not allow the contents of the reactor from entering the sleeves or tubes. The tubes can be secured within the reactor so that they remain in place throughout the use of the reactor. In certain embodiments, the tubes are secured to the wall of the reactor. The tubes can be secured to the wall through use of a suitable mechanical technique, or other conventional techniques for securing objects to one another. The materials used in the securing of the tubes is preferably inert and will not interfere with the operation of the reactor or negatively impact the purity of the water, or release contaminants into the water.

The lamps can be arranged within the reactor such that they are parallel to each other. The lamps can also be arranged within the reactor at various angles to one another. For example, in certain embodiments, the lamps can be arranged to illuminate paths or coverage regions that form an angle of approximately 90 degrees such that they are approximately orthogonal or perpendicular to one another. The lamps can be arranged in this fashion, such that they form an approximately 90 degree angle on a vertical axis or a horizontal axis, or any axis therebetween.

In certain embodiments, the reactor can comprise an array of tubes in the reactor or vessel comprising a first set of parallel tubes and a second set of parallel tubes. Each tube may comprise at least one ultraviolet lamp and each of the parallel tubes of the first set can be arranged to be at a desired angle relative to the second set of parallel tubes. The angle may be approximately 90 degrees in certain embodiments. The tubes of any one or both of the first array and the second array may extend across an inner volume of the reactor. The tubes of the first set and the second set can be arranged at approximately the same elevation within the reactor.

Further configurations can involve tubes and/or lamps that are disposed to provide a uniform level of intensity at respective occupied or coverage regions in the reactor. Further configurations can involve equispacially arranged tubes with one or more lamps therein.

The reactor may contain one or more arrays of tubes arranged within the reactor or vessel. A second array of tubes can comprise a third set of parallel tubes, and a fourth set of parallel tubes orthogonal to the third set of parallel tubes, each tube comprising at least one ultraviolet lamp. The fourth set of parallel tubes can also be orthogonal to at least one of the second set of parallel tubes and the first set of parallel tubes.

In certain embodiments, each array within the reactor or vessel can be positioned a predetermined distance or elevation from another array within the reactor. The predetermined distance between a set of two arrays can be the same or different.

The reactor can be sized based on the number of ultraviolet lamps required to scavenge, degrade, or otherwise convert at least one of the impurities, typically the organic carbon-based impurities into an inert, ionized, or otherwise removable compound, one or more compounds that may be removed from the water, or at least to one that can be more readily removed relative to the at least one impurity. The number of lamps required can be based at least in part on lamp performance characteristics including the lamp intensity and spectrum wavelengths of the ultraviolet light emitted by the lamps. The number of lamps required can be based at least in part on at least one of the expected TOC concentration or amount in the inlet water stream and the amount of oxidant added to the feed stream or reactor.

Sets of serially arranged reactors can be arranged in parallel. For example, a first set of reactors in series may be placed in parallel with a second set of reactors in series, with each set having three reactors, for a total of six reactors. Any one or more of the reactors in each set may be in service at any time. In certain embodiments, all reactors may be in service, while in other embodiments, only one set of reactors is in service.

One non-limiting example of an actinic radiation reactor vessel that may be utilized in aspects and embodiments disclosed herein is illustrated in FIG. 1, generally at 100. Reactor vessel 100 typically comprises inlet 110, outlet 120, and baffle 115 which divides reactor vessel 100 into upper chamber 125 and lower chamber 130. Reactor vessel 100 can also comprise manifold 105 which can be configured to distribute water introduced through inlet 110 throughout the vessel. In certain embodiments, manifold 105 can be configured to evenly distribute water throughout the vessel. For example, manifold 105 can be configured to evenly distribute water throughout the vessel such that the reactor operates as a plug flow reactor.

In some embodiments, the reactor vessel may comprise more than one baffle 115 to divide the reactor vessel into more than two chambers. Baffle 115 can be used to provide mixing or turbulence to the reactor. In certain embodiments, as shown in FIG. 1, reactor inlet 110 is in fluid communication with lower chamber 130 and reactor outlet 120 is in fluid communication with upper chamber 125.

In some embodiments, at least three reactor chambers, each having at least one ultraviolet (UV) lamp disposed to irradiate the water in the respective chambers with light of about or ranging from about 185 nm to about 254 nm, 220 nm, and/or 254 nm at a desired or at various power levels, are serially arranged in reactor 120.

The reactor vessel can also comprise a plurality of ultraviolet lamps positioned within tubes, for example, tubes 135a-c and 140a-c. In one embodiment, as shown in FIG. 1, reactor vessel 100 comprises a first set of parallel tubes, tubes 135a-c and a second set of parallel tubes (not shown). Each set of parallel tubes of the first set is approximately orthogonal to the second set to form first array 145. Tubes 135a-c and the second set of parallel tubes are at approximately the same elevation in reactor vessel 100, relative to one another.

Further, the reactor vessel can comprise a third set of parallel tubes and a fourth set of parallel tubes. Each set of parallel tubes of the first set is approximately orthogonal to the second set to form, for example, second array 150. As exemplarily illustrated, tubes 140a-c and the second set of parallel tubes are at approximately the same elevation in reactor vessel 100, relative to one another. As shown in FIG. 1, first array 145 can be positioned at a predetermined distance from second array 150. Vessel 100 can additionally comprise third array 155 and fourth array 160, each optionally having similar configurations as first array 140 and second array 145.

Figure 2A:
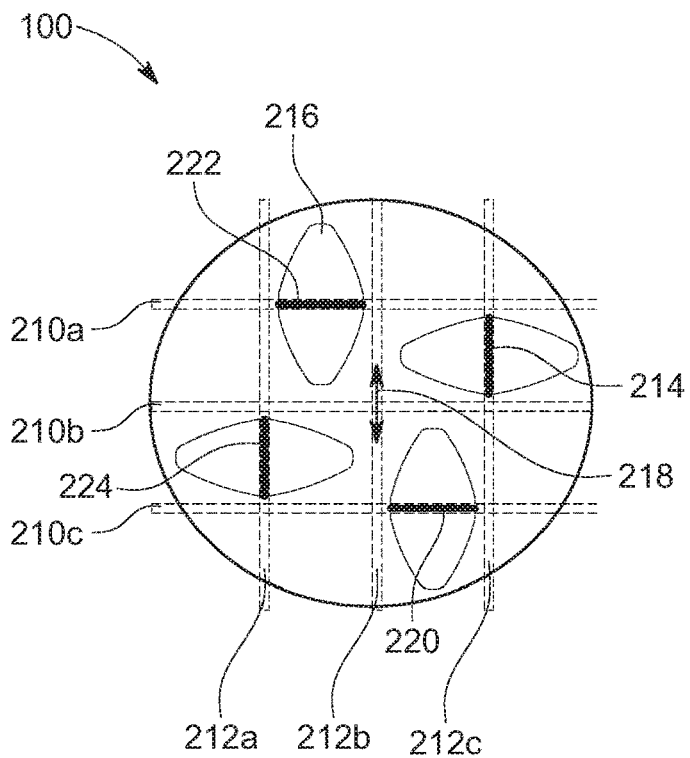
FIG. 2A is a schematic drawing illustrating a portion of an interior of the vessel of FIG. 1 in accordance with one or more embodiments.

In another embodiment, a first tube 135b can be arranged orthogonal to a second tube 140b to form a first array. Additionally, a set of tubes, tube 165a and tube 165b can be arranged orthogonal to another set of tubes, tube 170a and tube 170b to form a second array. The position of the lamps of the second array are shown in FIG. 2A, including lamps 214, 220, 222, and 224. The positions of the lamps in the first array and the second array are shown in FIG. 2B, including lamps 226 and 228 of the first array and lamps 214, 220, 222, and 224 of the second array.

The lamps can generate a pattern, depending on various properties of the lamp, including the dimensions, intensity, and power delivered to the lamp. The light pattern generated by the lamp is the general volume of space to which that the lamp emits light. In certain embodiments the light pattern or illumination volume is defined as the area or volume of space that the lamp can irradiate or otherwise provide actinic radiation to and allow for division or conversion of the precursor compound into the one or more free radical species.

Figure 2B:
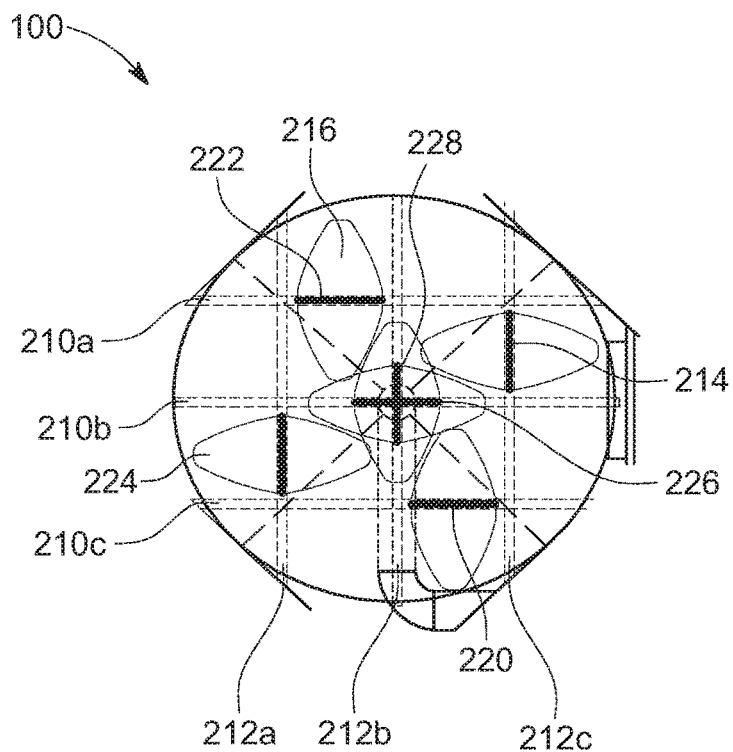
FIG. 2B is a schematic drawing illustrating another portion of an interior of the vessel of FIG. 1 in accordance with one or more embodiments.

As shown in FIGS. 2A and 2B, which shows exemplarily cross-sectional views of reactor 100, a first set of tubes 210a-c are arranged parallel to one another, and a second set of tubes 212a-c are arranged parallel to one another. As shown, first set of tubes 210a-c is arranged orthogonal relative to second set of tubes 212a-c. Lamps, such as lamps 214, are dispersed within tubes 210a-c and 212a-c, and when illuminated, can generate light pattern 216.

One or more ultraviolet lamps, or a set of lamps, can be characterized as projecting actinic radiation parallel to an illumination vector. The illumination vector can be defined as a direction in which one or more lamps emits actinic radiation. In an exemplarily embodiment, as shown in FIG. 2A, a first set of lamps, including lamp 220 and 222, is disposed to project actinic radiation parallel to illumination vector 218.

A first set of ultraviolet lamps, each of which is disposed to project actinic radiation parallel to a first illumination vector, can be energized. A second set of ultraviolet lamps, each of which is disposed to project actinic radiation parallel to a second illumination vector, can also be energized. At least one of the direction of the illumination and the intensity of at least one of the first set of ultraviolet lamps and second set of ultraviolet lamps can be adjusted. Each set of ultraviolet lamps can comprise one or more ultraviolet lamps.

The number of lamps utilized or energized and the configuration of the lamps in use can be selected based on the particular operating conditions or requirements of the system. For example, the number of lamps utilized for a particular process can be selected and controlled based on characteristics or measured or calculated parameters of the system. For example, measured parameters of the inlet water or treated water can include any one or more of TOC concentration, temperature, or flow rate. The number of energized lamps can also be selected and controlled based on the concentration or amount of oxidant, e.g., hydrogen peroxide added to the system. For example, 12 lamps in a particular configuration can be used if the flow rate of the water to be treated is at or below a certain threshold value, for example, a nominal or design flow rate, such as 1300 gpm, while more lamps can be used if the flow rate of the water to be treated rises above the threshold value. For example, if the flow rate increases from 1300 gpm to a selected higher threshold value, additional lamps can be energized. For example, 24 lamps may be used if the flow rate of the water to be treated reaches 1900 gpm. Thus, the flow rate of the water can be partially determinative of which lamps and/or the number of energized lamps in each reactor.

In certain embodiments, the ultraviolet lamps can be operated at one or more illumination intensity levels. For example, one or more lamps can be used that can be adjusted to operate at a plurality of illumination modes, such as at any of dim, rated, and boost mode, for example, a low, medium, or high mode. The illumination intensity of one or more lamps can be adjusted and controlled based on characteristics or measured or calculated parameters of the system, such as measured parameters of the inlet water or treated water, including TOC concentration, temperature, and/or flow rate. The illumination intensity of one or more lamps can also be adjusted and controlled based on the concentration or amount of hydrogen peroxide added to the system. For example, the one or more lamps can be used in a dim mode up to a predetermined threshold value of a measured parameter of the system, such as a first TOC concentration. The one or more lamps can be adjusted to rated mode if the measured or calculated TOC concentration reaches or is above a second TOC concentration, which may be above the threshold value. The one or more lamps can further be adjusted to a boost mode if the measured or calculated TOC concentration reaches or is above a second threshold value.

Actinic radiation reactors that may be utilized in systems disclosed herein are described in further detail in commonly owned PCT application No. PCT/US2016/030708 which is incorporated in its entirety herein by reference.

Figure 3:
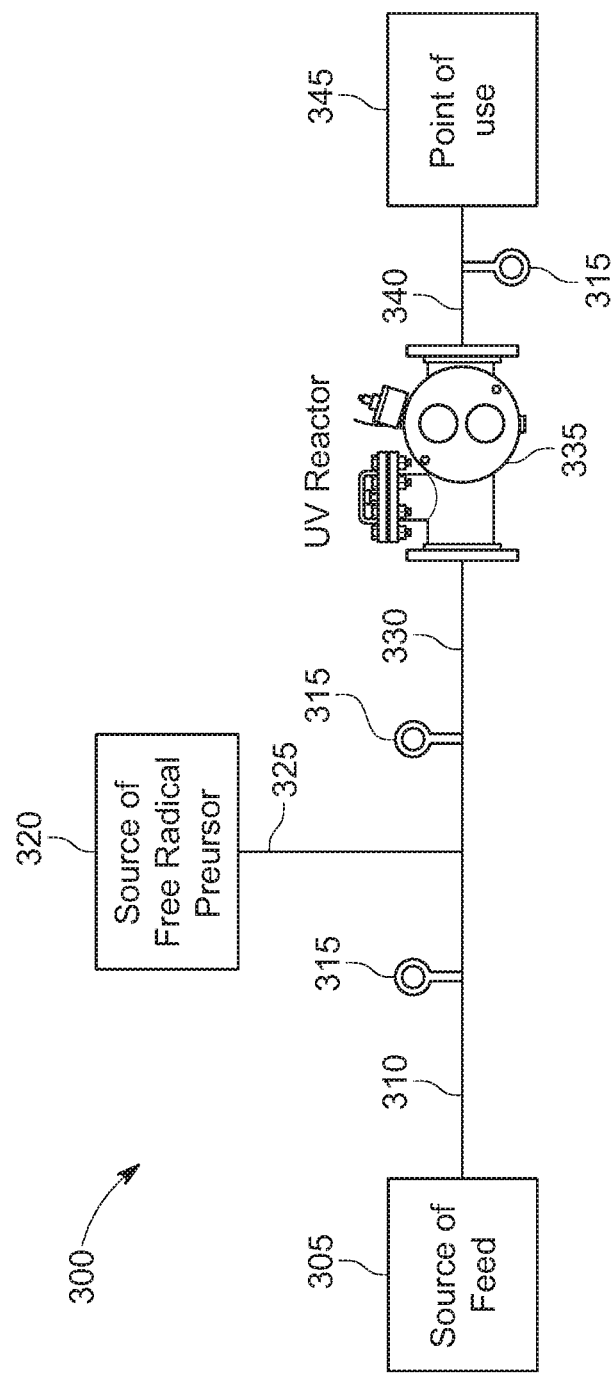
FIG. 3 illustrates an embodiment of system including an actinic radiation reactor vessel and a source of a precursor for free radicals in communication with a source of water to be treated upstream of the actinic radiation reactor vessel.

An embodiment of a system for treatment of water is illustrated schematically in FIG. 3 and indicated generally at 300. Water to be treated, for example, wastewater, groundwater, high purity water, etc., is provided from a source of feed 305 into conduit 310. One or more precursors for one or more free radicals (e.g., $H_2O_2$ which is a precursor for hydroxide radicals or a persulfate salt which is a precursor for a sulfate radical) is provided from the source of free radical precursor 320 through conduit 325 and is mixed with the water to be treated from the source of feed 305. The water/precursor mixture is directed through a conduit 330 into an inlet of an UV AOP reactor 335. Contaminants in the water to be treated are oxidized and destroyed by exposure to UV radiation in the UV AOP reactor 335. The UV AOP reactor 335 outputs a purified effluent or product water 340 which is directed to a point of use 345. The effluent 340 may meet or exceed a desired purity. As the term is used herein, purity of the effluent or product water exiting the actinic radiation reactor refers to a concentration of one or more contaminants in the effluent or product water. In some embodiments, the point of use 345 may be the source of feed 305, for example, when the system is used to treat water from a swimming pool, boiler, or other source of water and returns the treated water to the same source. The point of use 345 may include a shipboard system, a drilling platform system, an aquatics system (for example, a swimming pool or a fountain), a drinking water system, or a downhole of an oil drilling system. The point of use 345 may include a cooling water system of a ship or sea-based platform or a ballast tank of a ship.

One or more sensors 315 may measure one or more parameters, for example, temperature, flow rate, contaminant concentration, pH, oxidation-reduction potential (ORP), total organic carbon (TOC), dissolved oxygen and/or hydrogen concentration, purity, etc. of any of the water to be treated, water/precursor mixture, and/or purified effluent 340. A controller of the system, described further below, may receive readings from the one or more sensors 315 and adjust one or more operating parameters of the system to obtain a desired level of a parameter or parameters read by the one or more sensors 315. The operating parameters of the system may include, for example, intensity of UV light produced in the UV AOP reactor, dosage of UV radiation applied to water to be treated in the UV AOP reactor, flow rate of the water to be treated, rate or amount of addition of the free radical precursor to the water to be treated, or any other operating parameter of the system.

Various additional pumps or valves may be included in the system 300 to control flow of the various aqueous solutions involved, but are not illustrated for the purpose of clarity.

In one or more embodiments, any of which may be relevant to one or more aspects, the systems and techniques disclosed herein may utilize one or more subsystems that adjusts or regulates or at least facilitates adjusting or regulating at least one operating parameter, state, or condition of at least one unit operation or component of the system or one or more characteristics or physical properties of a process stream. To facilitate such adjustment and regulatory features, one or more embodiments may utilize controllers and indicative apparatus that provide a status, state, or condition of one or more components or processes. For example, at least one sensor may be utilized to provide a representation of an intensive property or an extensive property of, for example, water from the source of feed 305 or water entering or leaving the electrochemical cell or UV AOP reactor vessel or one or more other downstream processes. Thus, in accordance with a particularly advantageous embodiment, the systems and techniques may involve one or more sensors or other indicative apparatus, such as composition analyzers, or conductivity cells, that provide, for example, a representation of a state, condition, characteristic, or quality of the water entering or leaving any of the unit operations of the system.

Various operating parameters of the system 300 disclosed herein may be controlled or adjusted by an associated control system or controller based on various parameters measured by various sensors located in different portions of the system. The controller may be programmed or configured to regulate introduction of free radical precursor into water to be treated upstream of an AOP reactor based at least on one or more of a flow rate of the water to be treated, or a level of one or more contaminants in the water to be treated.

The controller may be programmed or configured to regulate one or more operating parameters of the AOP reactor based on any one or more of flow rate or contaminant concentration of water to be treated entering the AOP reactor, or temperature or pH of the water to be treated entering the AOP reactor.

The controller used for monitoring and controlling operation of the various elements of systems disclosed herein may include a computerized control system. Various aspects of the controller may be implemented as specialized software executing in a general-purpose computer system 400 such as that shown in FIG. 4. The computer system 400 may include a processor 402 connected to one or more memory devices 404, such as a disk drive, solid state memory, or other device for storing data. Memory 404 is typically used for storing programs and data during operation of the computer system 400. Components of computer system 400 may be coupled by an interconnection mechanism 406, which may include one or more busses (e.g., between components that are integrated within a same machine) and/or a network (e.g., between components that reside on separate discrete machines). The interconnection mechanism 406 enables communications (e.g., data, instructions) to be exchanged between system components of system 400. Computer system 400 also includes one or more input devices 408, for example, a keyboard, mouse, trackball, microphone, touch screen, and one or more output devices 410, for example, a printing device, display screen, and/or speaker.

The output devices 410 may also comprise valves, pumps, or switches which may be utilized to introduce a precursor for a free radical species from the source of free radical precursor 320 into the water to be treated and/or to control the speed of pumps or the state (open or closed) of valves of systems as disclosed herein. One or more sensors 414 may also provide input to the computer system 400. These sensors may include, for example, sensors 315 which may be, for example, pressure sensors, chemical concentration sensors, temperature sensors, or sensors for any other parameters of interest to the systems disclosed herein. These sensors may be located in any portion of the system where they would be useful, for example, upstream of point of use 345 or AOP reactor 335, or in fluid communication with source of feed 305. In addition, computer system 400 may contain one or more interfaces (not shown) that connect computer system 400 to a communication network in addition or as an alternative to the interconnection mechanism 406.

Figure 5:
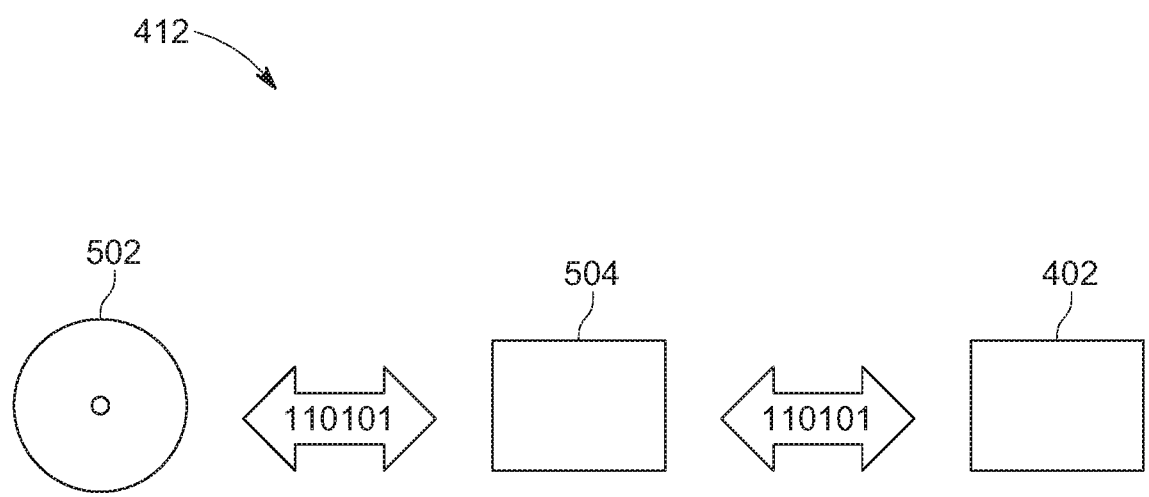
FIG. 5 illustrates a memory system for the control system of FIG. 4.

The storage system 412, shown in greater detail in FIG. 5, typically includes a computer readable and writeable nonvolatile recording medium 502 in which signals are stored that define a program to be executed by the processor 402 or information to be processed by the program. The medium may include, for example, a disk or flash memory. Typically, in operation, the processor causes data to be read from the nonvolatile recording medium 502 into another memory 504 that allows for faster access to the information by the processor than does the medium 502. This memory 504 is typically a volatile, random access memory such as a dynamic random access memory (DRAM) or static memory (SRAM). It may be located in storage system 412, as shown, or in memory system 404. The processor 402 generally manipulates the data within the integrated circuit memory 504 and then copies the data to the medium 502 after processing is completed. A variety of mechanisms are known for managing data movement between the medium 502 and the integrated circuit memory element 504, and aspects and embodiments disclosed herein are not limited thereto. Aspects and embodiments disclosed herein are not limited to a particular memory system 404 or storage system 412.

The computer system may include specially-programmed, special-purpose hardware, for example, an application-specific integrated circuit (ASIC). Aspects and embodiments disclosed herein may be implemented in software, hardware or firmware, or any combination thereof. Further, such methods, acts, systems, system elements and components thereof may be implemented as part of the computer system described above or as an independent component.

Figure 4:
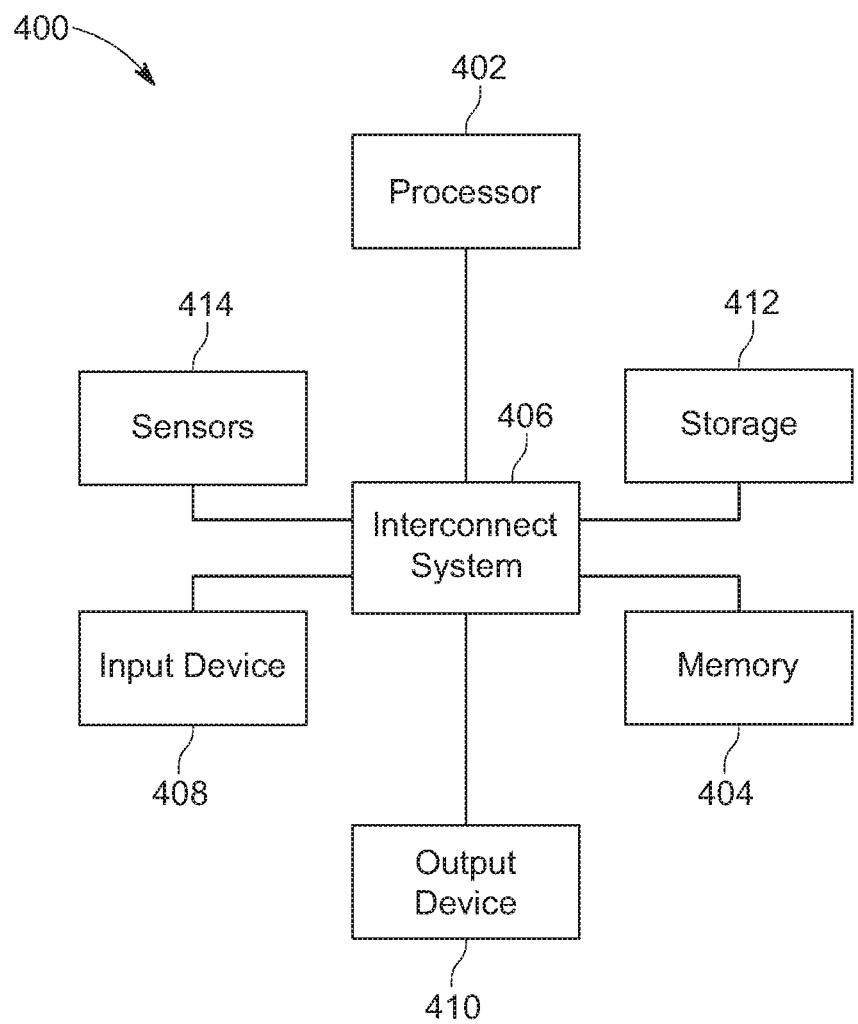
FIG. 4 illustrates a control system that may be utilized for embodiments of water treatment systems disclosed herein.

Although computer system 400 is shown by way of example as one type of computer system upon which various aspects and embodiments disclosed herein may be practiced, it should be appreciated that aspects and embodiments disclosed herein are not limited to being implemented on the computer system as shown in FIG. 4. Various aspects and embodiments disclosed herein may be practiced on one or more computers having a different architecture or components than shown in FIG. 4.

Computer system 400 may be a general-purpose computer system that is programmable using a high-level computer programming language. Computer system 400 may be also implemented using specially programmed, special purpose hardware.

In computer system 400, processor 402 is typically a commercially available processor such as the well-known Pentium™ or Core™ class processors available from the Intel Corporation. Many other processors are available, including programmable logic controllers. Such a processor usually executes an operating system which may be, for example, the Windows 7, Windows 8, or Windows 10 operating system available from the Microsoft Corporation, the MAC OS System X available from Apple Computer, the Solaris Operating System available from Sun Microsystems, or UNIX available from various sources. Many other operating systems may be used.

The processor and operating system together define a computer platform for which application programs in high-level programming languages are written. It should be understood that the invention is not limited to a particular computer system platform, processor, operating system, or network. Also, it should be apparent to those skilled in the art that aspects and embodiments disclosed herein are not limited to a specific programming language or computer system. Further, it should be appreciated that other appropriate programming languages and other appropriate computer systems could also be used.

One or more portions of the computer system may be distributed across one or more computer systems (not shown) coupled to a communications network. These computer systems also may be general-purpose computer systems. For example, various aspects of the invention may be distributed among one or more computer systems configured to provide a service (e.g., servers) to one or more client computers, or to perform an overall task as part of a distributed system. For example, various aspects and embodiments disclosed herein may be performed on a client-server system that includes components distributed among one or more server systems that perform various functions according to various aspects and embodiments disclosed herein. These components may be executable, intermediate (e.g., IL) or interpreted (e.g., Java) code which communicate over a communication network (e.g., the Internet) using a communication protocol (e.g., TCP/IP). In some embodiments one or more components of the computer system 400 may communicate with one or more other components over a wireless network, including, for example, a cellular telephone network.

It should be appreciated that the aspects and embodiments disclosed herein are not limited to executing on any particular system or group of systems. Also, it should be appreciated that the aspects and embodiments disclosed herein are not limited to any particular distributed architecture, network, or communication protocol. Various aspects and embodiments disclosed herein are may be programmed using an object-oriented programming language, such as SmallTalk, Java, C++, Ada, or C# (C-Sharp). Other object-oriented programming languages may also be used. Alternatively, functional, scripting, and/or logical programming languages may be used, for example, ladder logic. Various aspects and embodiments disclosed herein may be implemented in a non-programmed environment (e.g., documents created in HTML, XML or other format that, when viewed in a window of a browser program, render aspects of a graphical-user interface (GUI) or perform other functions). Various aspects and embodiments disclosed herein may be implemented as programmed or non-programmed elements, or any combination thereof.

Figure 6:
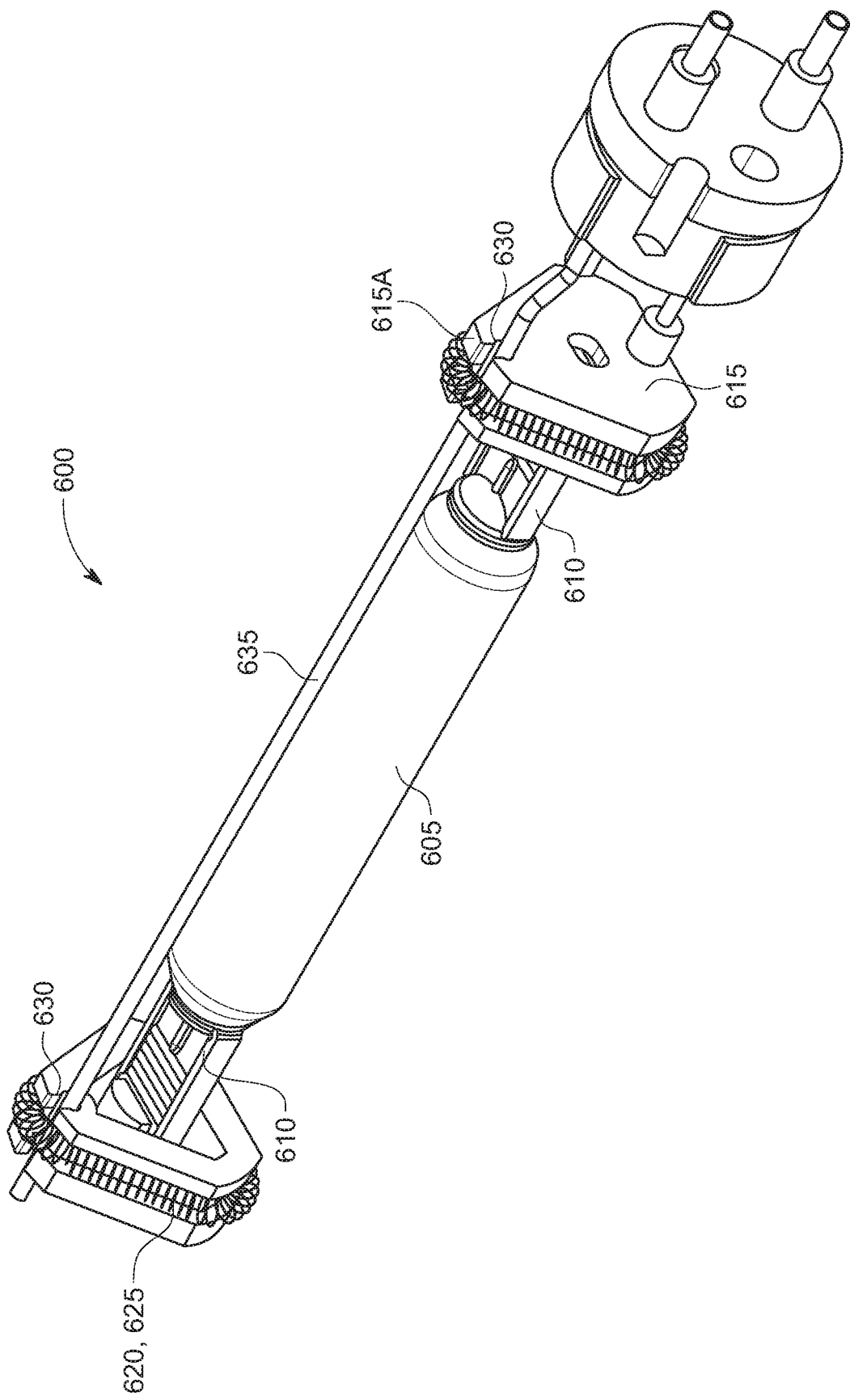
FIG. 6 illustrates an example of an ultraviolet (UV) lamp assembly.

An example of a UV lamp that may be utilized in a UV AOP reactor as disclosed herein is illustrated in FIG. 6, indicated generally at 600. The UV lamp 600 is a gas-discharge lamp having a sealed lamp tube 605. The lamp tube 605 is formed of a material that is transparent, or at least partially transparent to UV radiation, for example, quartz. The lamp tube 605 contains a gas that emits ultraviolet radiation when excited by electric current provided by electrodes (not shown) disposed at opposite ends within the lamp tube 605. The gas may include mercury vapor which may be mixed with one or more of neon, argon, and/or xenon. Commercially available UV lamps may be obtained from Alphacure (Northamptonshire, UK), Signify (Philips Lighting, The Netherlands), Heraeus Noblelight GmbH (Hanan, Germany), or Light Sources (LSI, Orange, Conn.).

Extending from opposite ends of the lamp tube 605 are sections of quartz 610 having generally rectangular or I-shaped cross-sections. These sections of quartz 610 are referred to as pinches 610. The pinches 610 include electrical conductors for bringing electrical current from external electrical connections to the electrodes within the lamp tube 605.

The pinches 610 are mounted within and secured by an adhesive or cement, for example, ceramic adhesive paste (available from Fortafix, Hartlepool, UK) within central portions of end caps 615 disposed on opposite sides of the lamp tube 605 at distal ends of the pinches 610 opposite proximal ends of the pinches 610 which contact the lamp tube 605. The end caps 615 are formed of a ceramic material, for example, alumina ($Al_2O_3$) or a mixture of primarily alumina and one or more other ceramic materials, for example, 95% $Al_2O_3$, CaO (1%), $SiO_2$ (2%), and MgO (2%). The end caps 615 may have a substantially triangular cross-section as illustrated in FIG. 6 in which the vertices of the triangular cross-section are truncated and replaced by arcuate tip portions 615A. The arcuate tip portions 615A may have outer surfaces defining portions of circle. The end caps 615 may also be considered to include three lobes extending outward from central regions of the end caps 615 and terminating in the arcuate tip portions 6125A. The triangular shape of the end caps 615 may facilitate electrically connecting the UV lamp 600 to electrical connectors known in the art, for example, as disclosed in U.S. Pat. No. 8,876,359, the contents of which are incorporated herein by reference. In other embodiments, the end caps 615 may be circular or any other shape that provides for the end caps 615 to fit within a quartz tube having a desired shape. The outer surfaces of the arcuate tip portions 6125A may be curved to match the curvature of an internal wall of a quartz tube in which the lamp tube 605 is to be disposed. The end caps 615 may this be considered to have portions of outer peripheral surfaces that are contoured to conform to an inner surface of the quartz tube.

Figure 7:
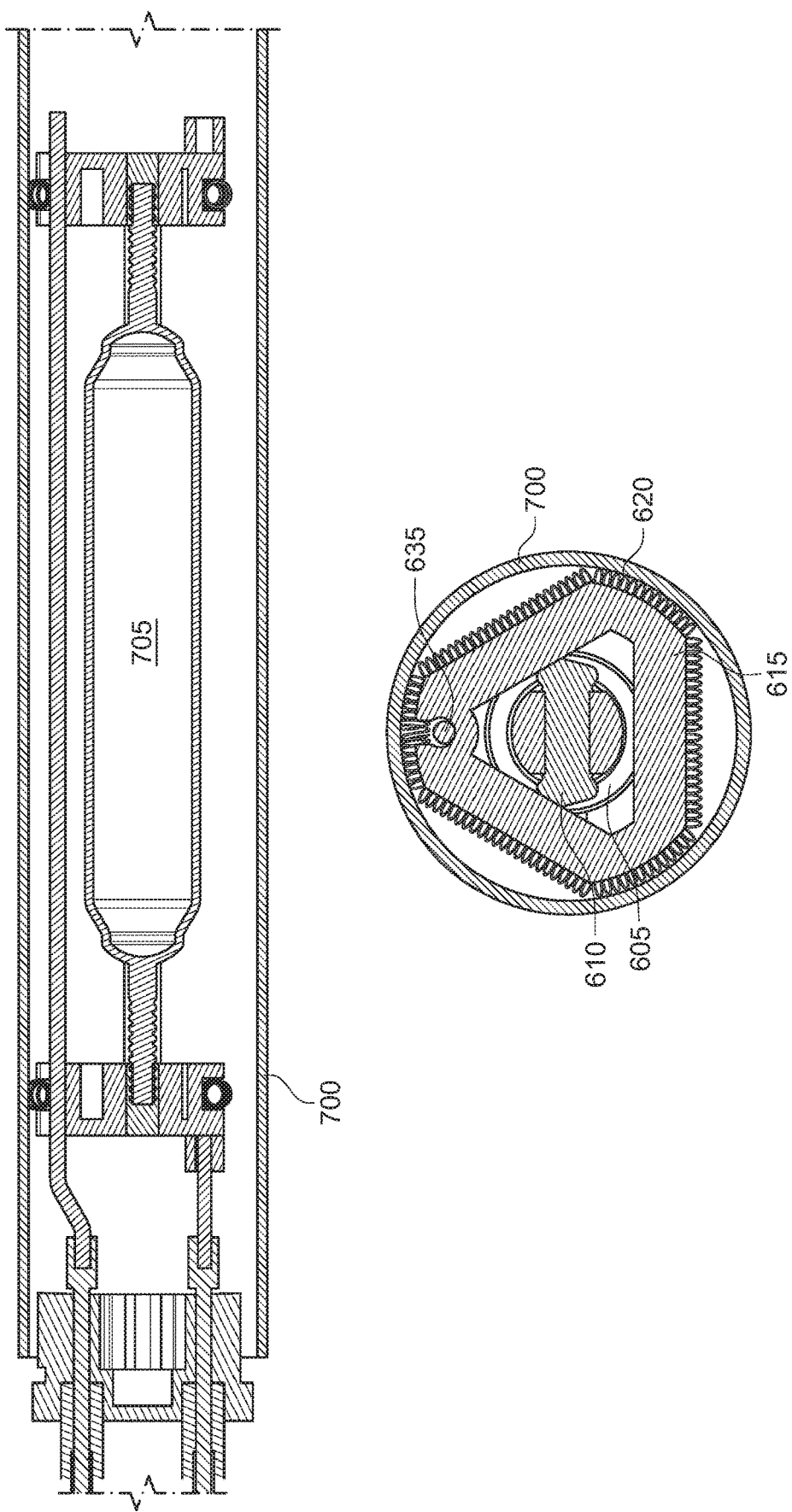
FIG. 7 illustrates the ultraviolet lamp assembly of FIG. 6 disposed within a quartz tube.

The end caps 615 may include thermally conductive biasing elements, for example, springs 620 (commercially available from iConn Engineering, Huntington Beach, Calif.) circumscribing their perimeters. As the term is used herein, "biasing" refers to supporting/positioning of the end caps and lamp tube 605 within a quartz tube. The thermally conductive biasing elements may also provide for the conduction heat from the end caps 615 to the quartz tube and may provide for vibration dampening for the lamp tube 605 within the quartz tube. In some embodiments, the springs 620 may be disposed within recesses 625 defined in the surfaces of the perimeter portions of the end caps 615. The springs 620 may be formed of coils canted at angles of, for example, about 70° relative to the surfaces of the perimeter portions of the end caps 615 to allow compression under radial load, aiding installation and reducing vibration. The springs 620 may be formed of a metal, for example, stainless steel. The springs 620 may provide for good contact between the lamp and a quartz tube in which the lamp may be installed, providing a high thermal conductivity path for heat transfer from the lamp tube 605 through the pinches 610 and end caps 615 to the quartz tube. The material of the end caps may have a thermal conductivity of about 15-25 W/m·K, while the ceramic adhesive may have a thermal conductivity of about 1.5 W/m·K and the spring may have a thermal conductivity of about 15 W/m·K. FIG. 7 illustrates, in both a cross-sectional and end view, how the UV lamp may be positioned within a quartz tube 700 with the lamp tube 605 centered coaxially within the quartz tube 700 and having a central axis parallel with or overlapping a central axis of the quartz tube 700. The quartz tube 700 may, in use, be submerged in water undergoing treatment in a UV reactor and may transfer heat into the water undergoing treatment which acts as a heat sink for the lamp assembly and helps cool the lamp assembly.

Slots 630 may be defined in the outer surfaces of the end caps 615, for example, in one of the arcuate tip portions 615A of one or both of the end caps 615 as illustrated in FIG. 6. An electrical conductor 635, for example, a metal rod used to provide current to one end of the lamp 600 may have portions disposed within the slots 630. The portions of the conductor 635 may be retained in the slots 630 by the springs 620. The slots 630 may provide for the conductor 635 to expand and to move slightly, for example, due to changes in temperature, thus reducing the stress that might be applied to the end caps 615 if the conductor 635 were instead fixedly secured in the end caps 615. It is to be understood that electrical connections to the lamp tube 605 are omitted from the diagrams presented herein for simplicity.

In some embodiments, an existing UV AOP system may be modified or upgraded to include UV lamps as disclosed herein, for example, as illustrated in FIGS. 6 and 7. A method of retrofitting a UV AOP system cell to increase the reliability of the system may include installing one or more UV lamps as disclosed herein in the UV AOP.

EXAMPLES

Vibrational Testing

Figure 8:
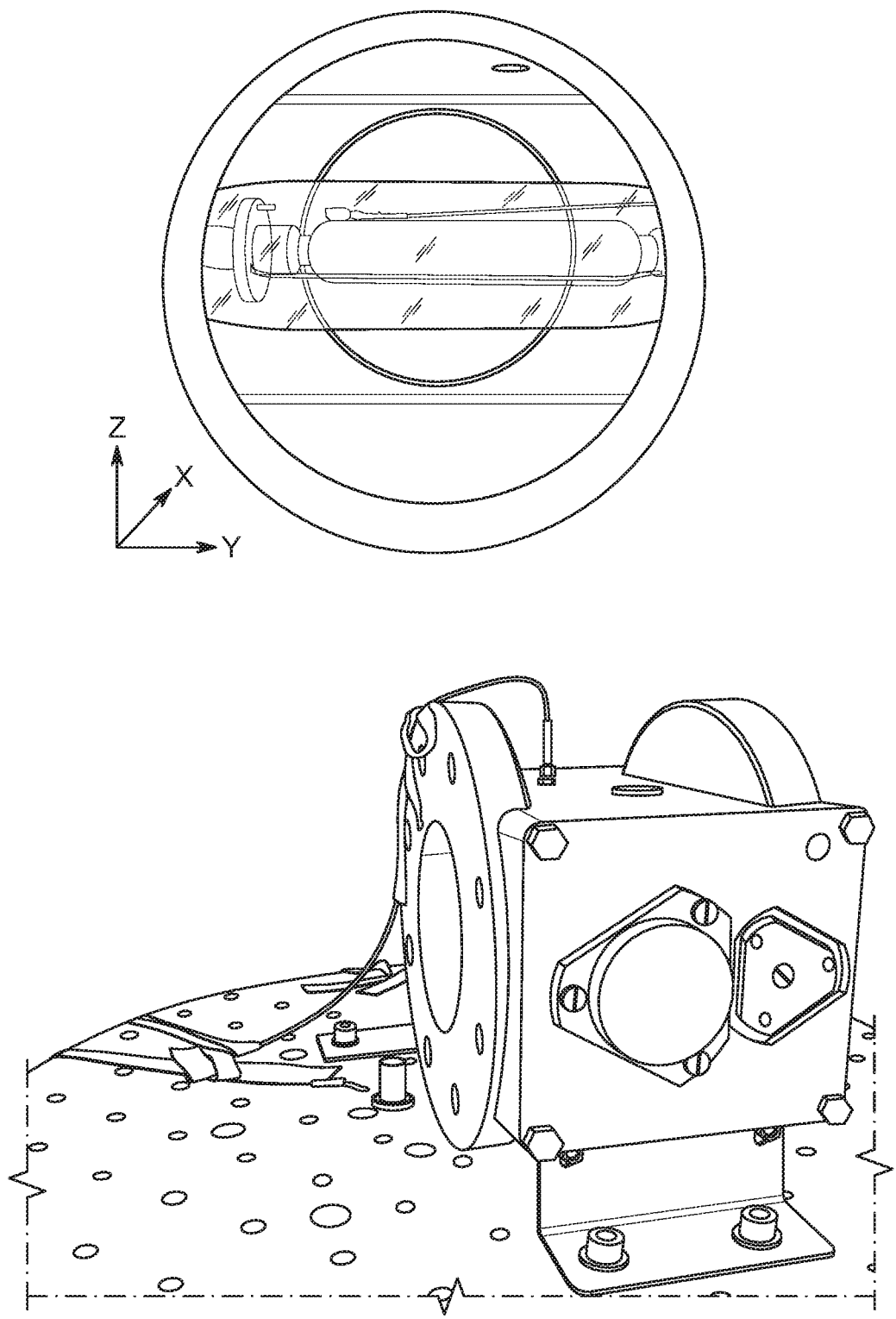
FIG. 8 illustrates an experimental setup for vibration testing of UV lamps.
Figure 9A:
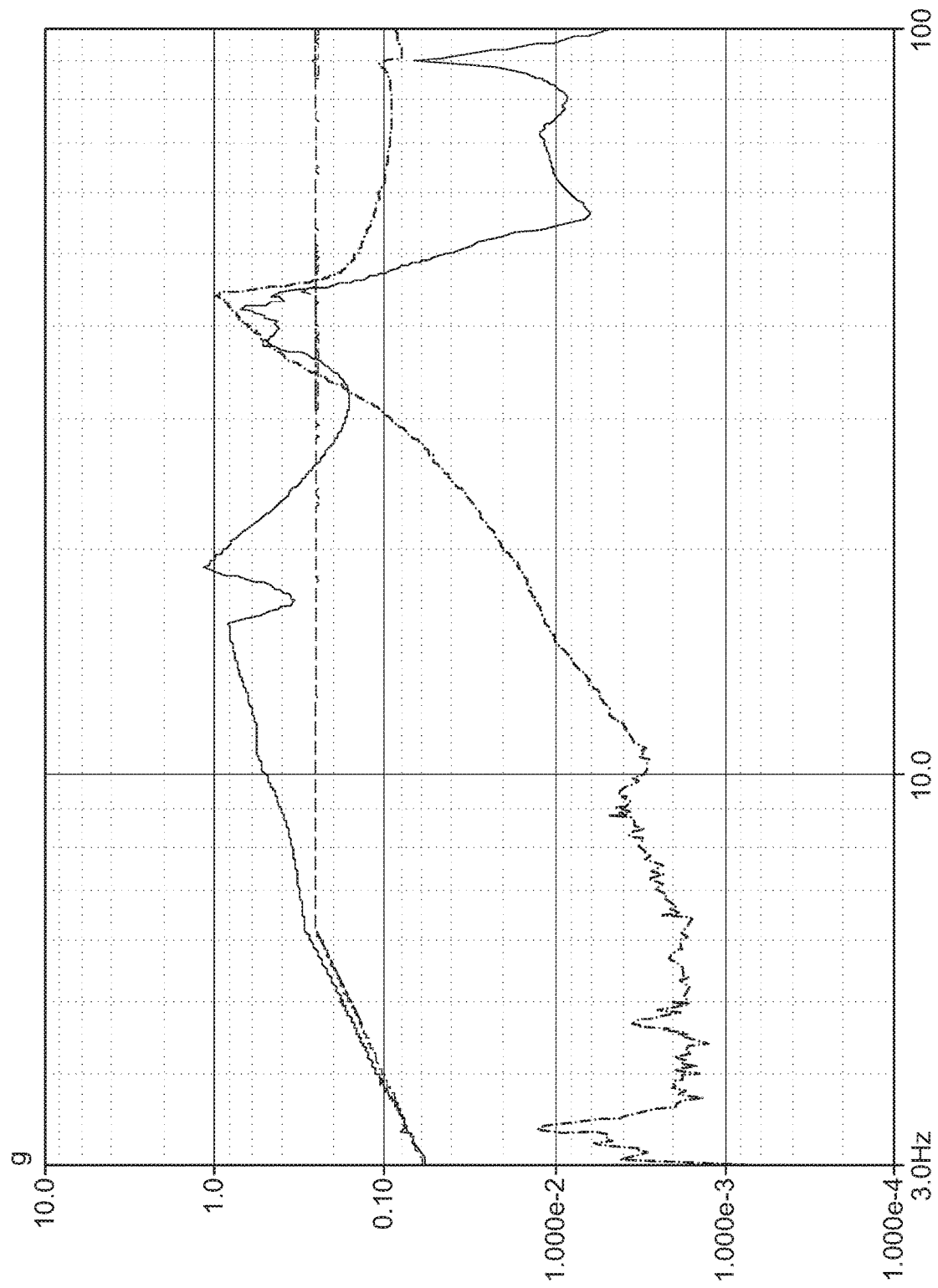
FIGS. 9A-9C illustrate results of vibration testing of a standard UV lamp.
Figure 9B:
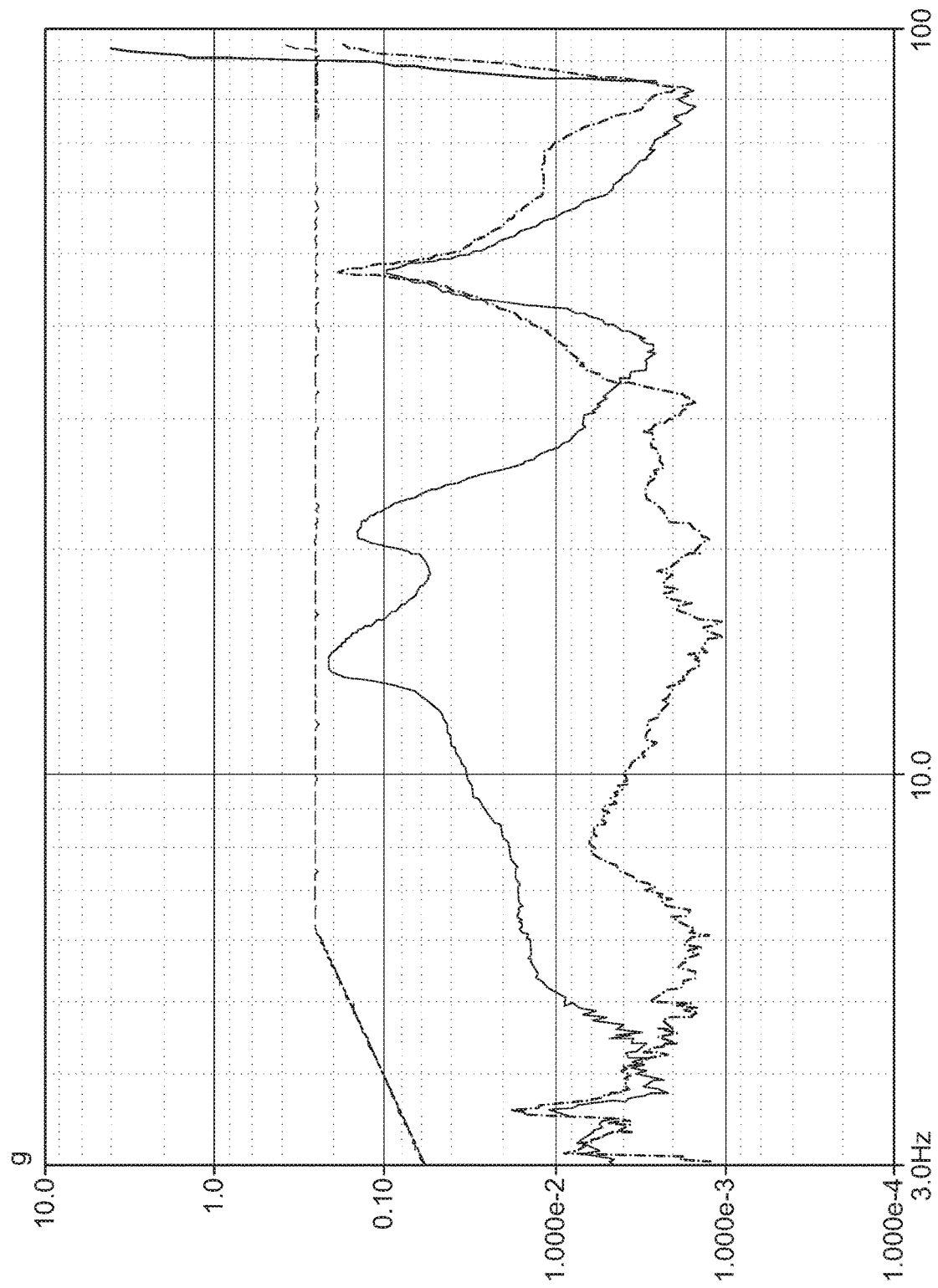
Figure 9C:
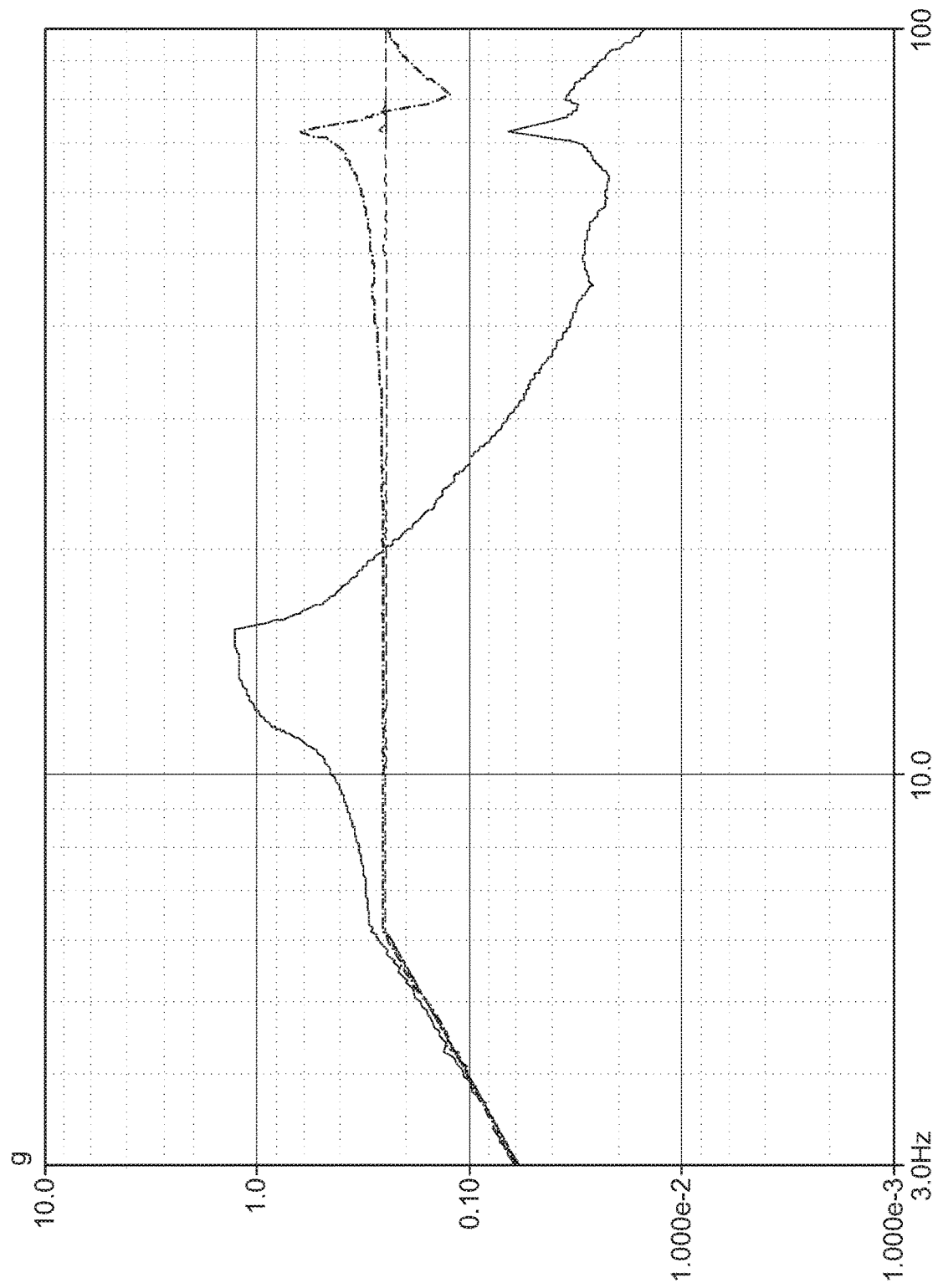

Tests were performed to evaluate the how lamps configured as disclosed herein (for example, as illustrated in FIGS. 6 and 7) responded to applied vibration as compared to standard lamps having circular end caps and that do not include springs circumscribing the end caps. The testing setup is illustrated in FIG. 8. Each lamp to was mounted in a UV reactor housing bolted to a vibration table and was tested six times; three directions (x, y, and z axes) and repeated after two hours of low-level vibration. FIGS. 9A-9C illustrate the results of the vibration testing of the standard lamps in the X, Y, and Z axes, respectively. In the charts of FIGS. 9A-9C, the Y axis represents recorded g-forces and the X axis represents applied vibrational frequency. There was little change between the initial and two hour sweeps, indicating that the lamp does not move or 'settle' after install. There are significant peaks in lamp resonance outside of the control at high magnitudes, where it is expected most damage would be done to the lamp.

Figure 10A:
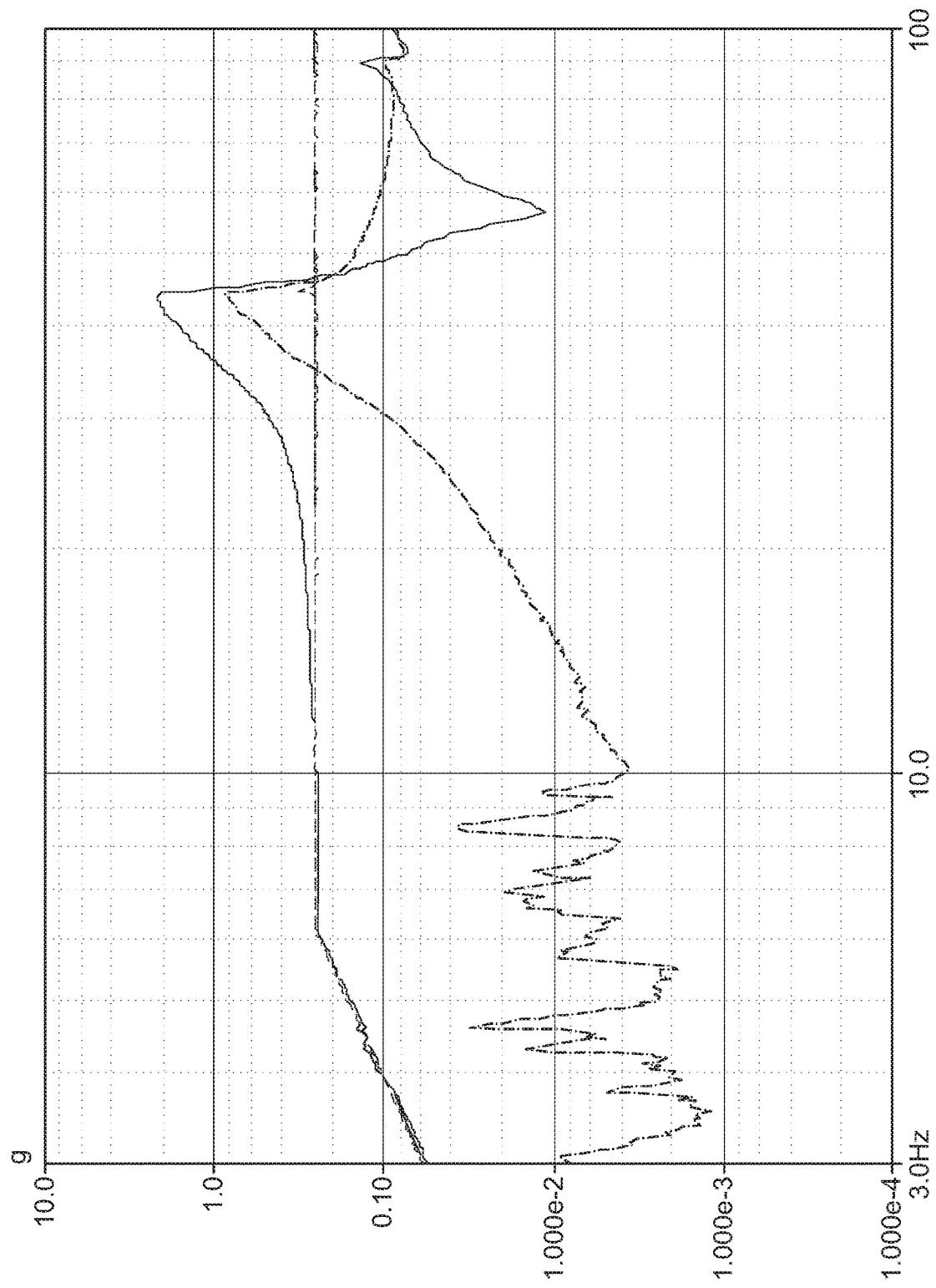
FIGS. 10-10C illustrate results of vibration testing of a UV lamp as illustrated in FIG. 6.
Figure 10B:
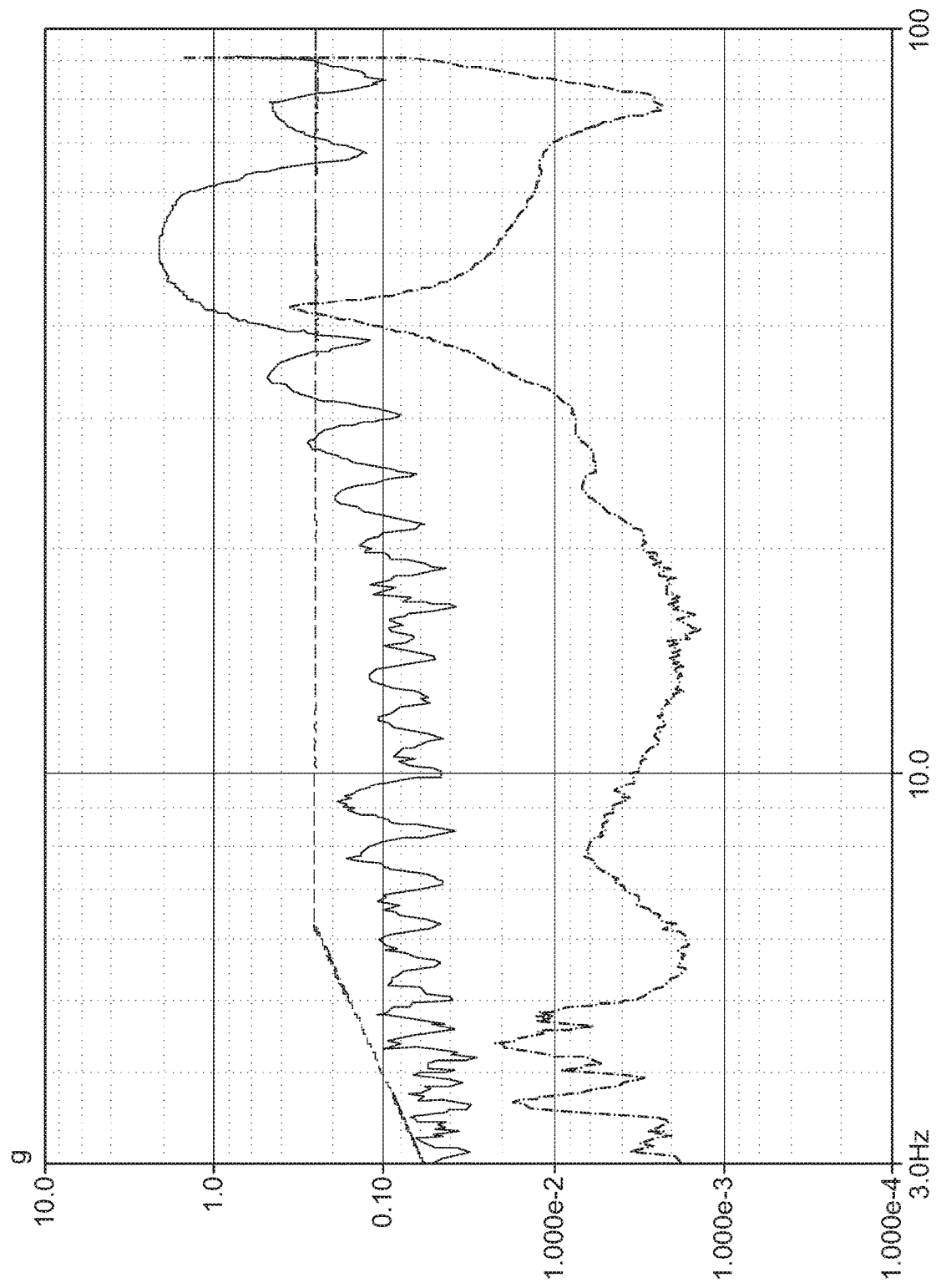
Figure 10C:
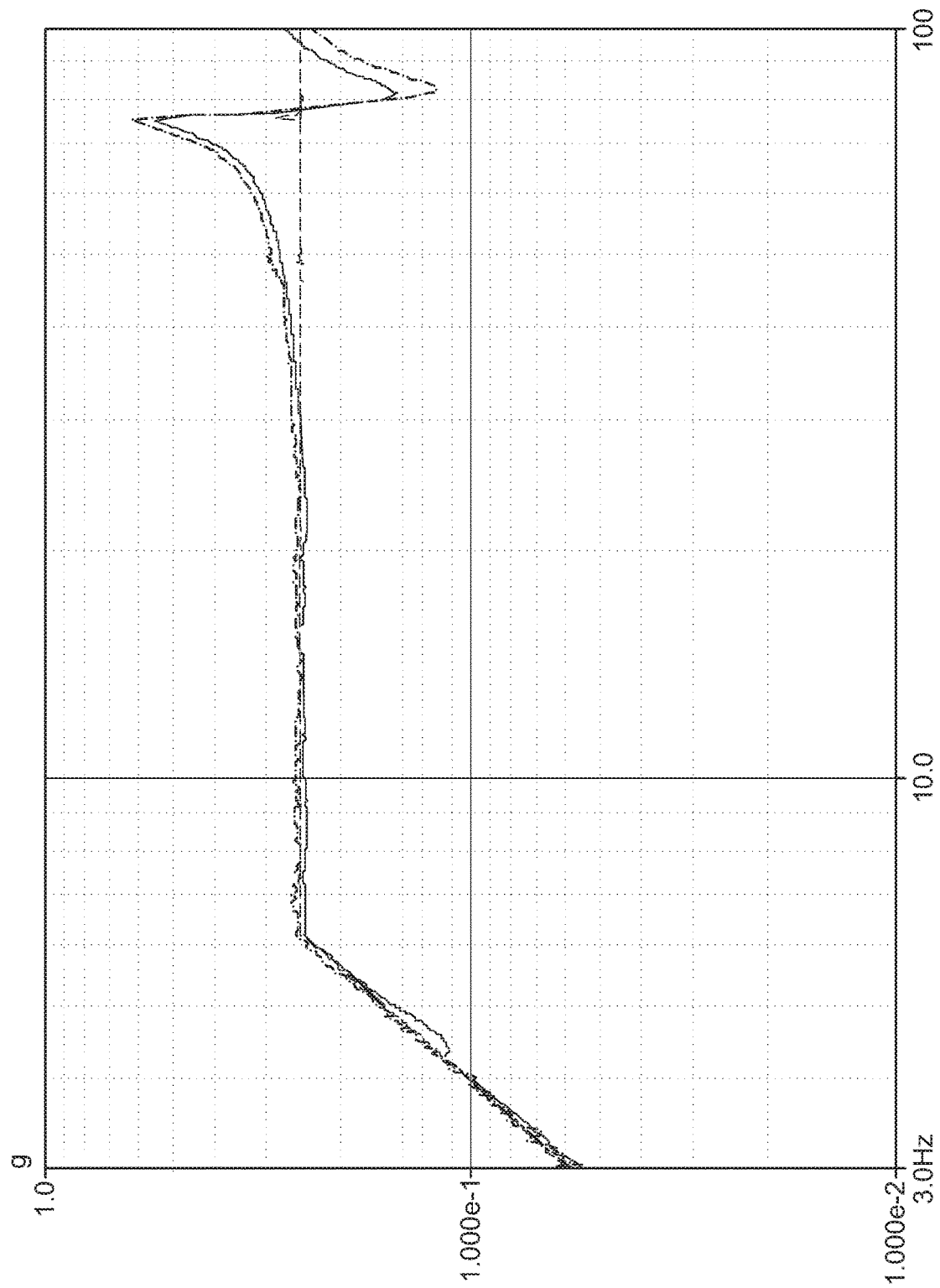

FIGS. 10A-10C illustrate the results of the vibration testing of the improved lamps configured as disclosed herein in the X, Y, and Z axes, respectively. There was little change between the initial and two hour sweeps, indicating that the lamp does not move or 'settle' after install. There are still peaks of resonance, however, the peaks are at lower magnitudes, and in general the lamp vibration much more closely matches the control. Lamps configured as disclosed herein were found to exhibit lower levels of vibration responsive to application of vibration from an external source as compared to standard lamps as shown by the reduced resonance magnitudes and frequency sweep response that more closely match the control.

The graphs in FIGS. 9A-10C show the response of various points of the test set up to the vibration applied. The lines representing the control are from a fixed point of the vibration bed, so essentially shows the frequency sweep being applied. The lines representing the vibration of the chamber, show similar response to the bed in the Z (vertical) direction but have their own separate response when in X or Y direction. The lines representing vibrations directly measured from the lamps housed within the chambers show the peaks in lamp resonance. The lamps are more resistant to lower frequency vibration, and the resonance peaks that were seen on the new lamp were generally at lower g-force levels.

Pinch Temperature Testing

One failure mode that was observed for standard lamps was breakage of the pinches. It was theorized that this failure mode was due to the thermal cycling of the pinches and associated induced stress. UV lamps may run as hot as 1000° C. and thus may cause significant thermally induced stresses in the pinches when turning on or off. Testing as performed to determine if UV lamps configured as disclosed herein (for example, as illustrated in FIGS. 6 and 7) could help reduce the variation in temperature observed in the pinches as compared to standard UV lamps.

Figure 11A:
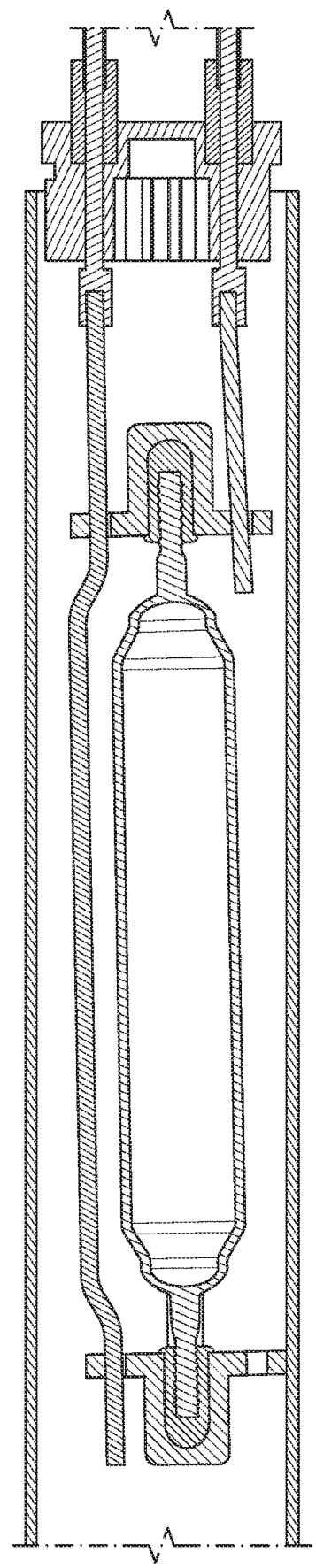
FIG. 11A illustrates a mounting configuration of a standard UV lamp in a quartz tube.
Figure 11B:
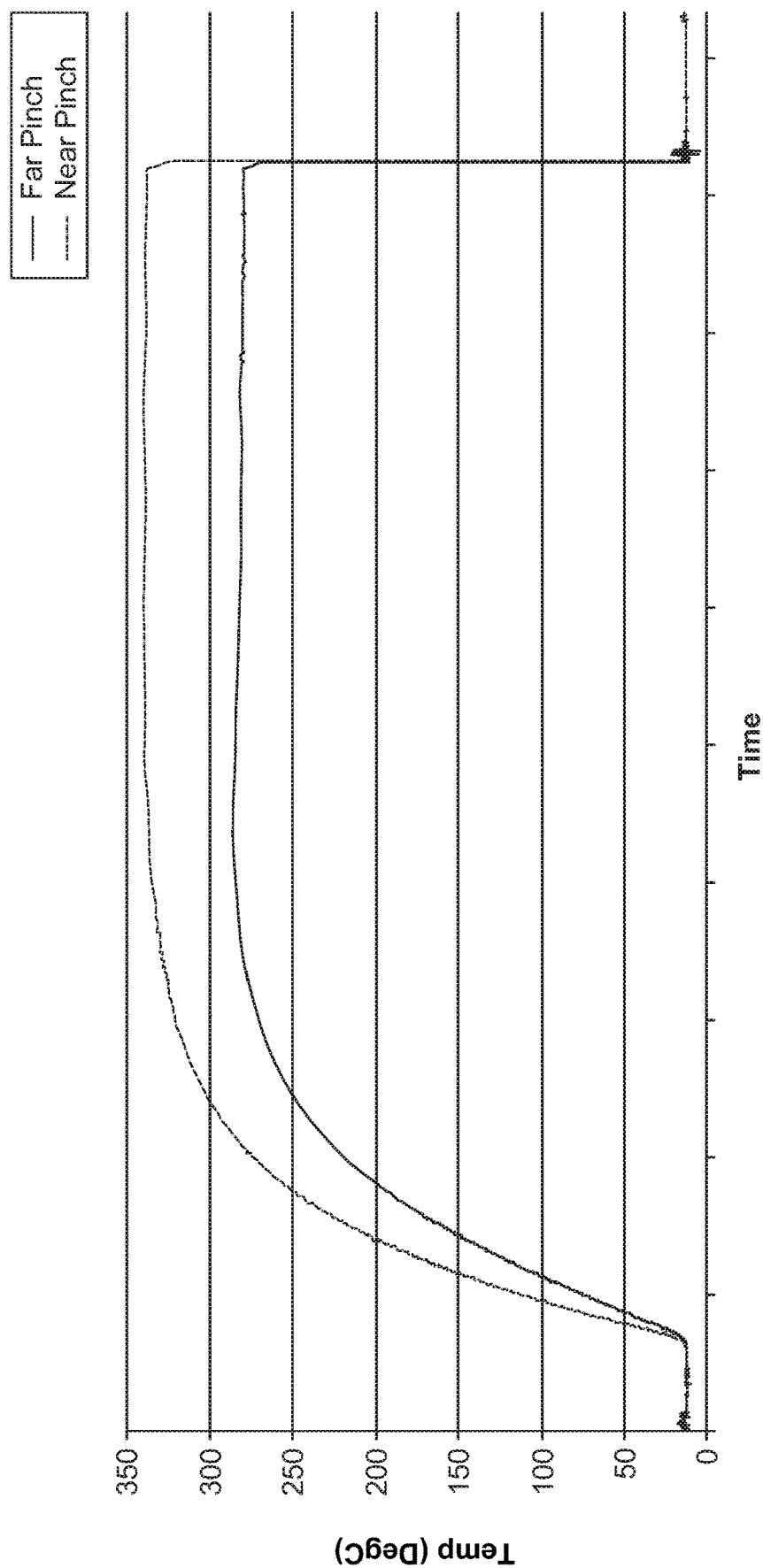
FIG. 11B illustrates operating temperatures of pinch portions of the standard UV lamp mounted as illustrated in FIG. 11A.

FIG. 11A illustrates one example of previously utilized mounting configuration of a standard UV lamp in a quartz tube. In this mounting configuration, the end cap closest to the electrical inputs was suspended within the quartz tube and did not contact the quartz tube. The end cap opposite the electrical inputs contacted the quartz tube on one side. FIG. 11B illustrates the variation in temperature of the "near pinch" mounted in the end cap closest to the electrical inputs and the "far pinch" mounted in the end cap opposite the electrical inputs over a period of 30 minutes after turning on the lamp when the quartz tube was submerged in water having a temperature of about 12° C. These results showed that there was roughly a 50° C. temperature difference between the near and far pinches, with the near pinch running at 340° C., and the far pinch running at 290° C. after the temperatures stabilized after the lamp was turned on. Without being bound to a particular theory, it is believed that this was due to the near end being suspended in air, whereas the far end has direct contact with the cooler quartz sleeve, as shown in FIG. 11A.

Figure 12A:
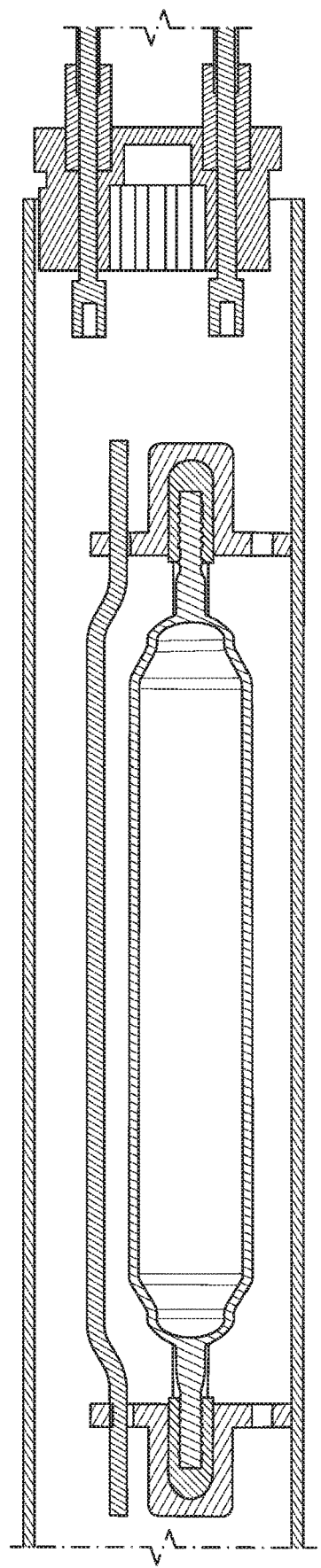
FIG. 12A illustrates another mounting configuration of a standard UV lamp in a quartz tube.
Figure 12B:
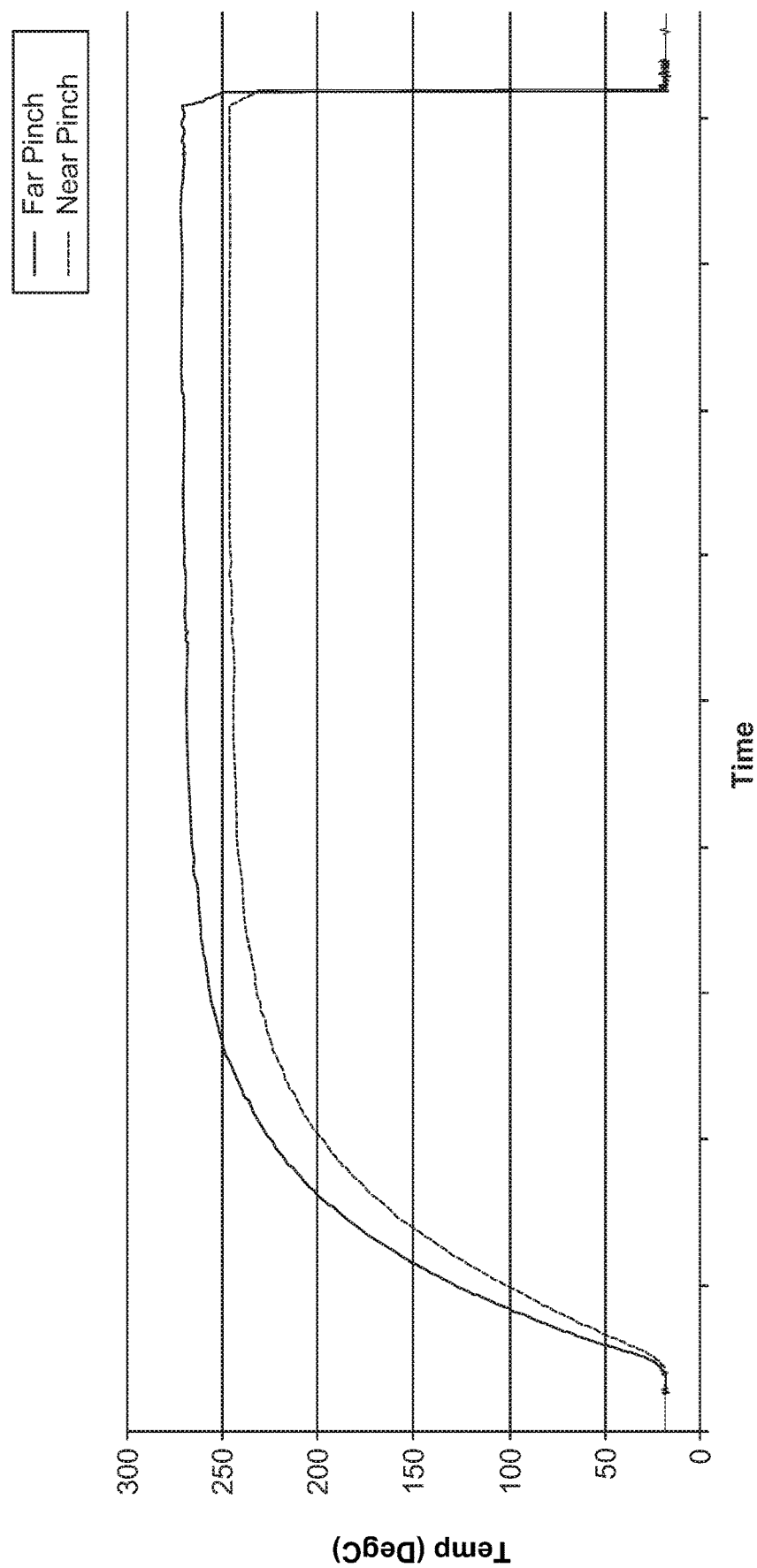
FIG. 12B illustrates operating temperatures of pinch portions of the standard UV lamp mounted as illustrated in FIG. 12A.

An alternate mounting configuration of a standard UV lamp is illustrated in FIG. 12A. In this configuration both the end cap closest to the electrical inputs and the end cap opposite the electrical inputs (including the "near pinch" and "far pinch", respectively) contacted the quartz tube on one side. Electrical connections to the lamp tube are omitted from this figure for clarity. FIG. 12B illustrates the variation in temperature of the "near pinch" and the "far pinch" in the mounting configuration of FIG. 12A over a period of 30 minutes after turning on the lamp when the quartz tube was submerged in water having a temperature of about 12° C. This data shows that when both ends are touching the sleeve, the overall temperatures seen are reduced (270° C. at the near end, 240° C. at the far end) when compared to the previous test, with the near end reduced by ~75° C., and the far end reduced by ~25° C. There is also less of a difference between the near and far end (20° C. rather than 50° C.).

Figure 13:
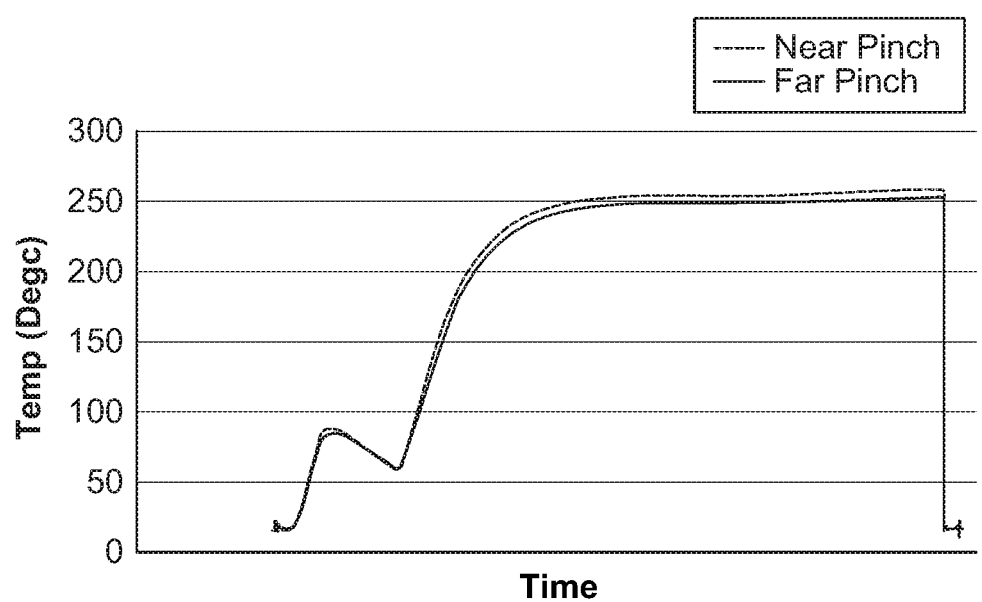
FIG. 13 illustrates operating temperatures of pinch portions of a UV lamp mounted as illustrated in FIG. 7.

In a further test, a lamp configured as disclosed herein was mounted in a quartz tube as illustrated in FIG. 7, described above. FIG. 13 illustrates the variation in temperature of the "near pinch" and the "far pinch" in the mounting configuration of FIG. 7 over a period of 30 minutes after turning on the lamp when the quartz tube was submerged in water having a temperature of about 12° C. The initial bump on the graph of FIG. 13 is due to the lamp being inadvertently stopped and restarted. FIG. 13 illustrates that with a lamp configured as disclosed herein, the pinches on both ends of the lamp tube exhibit very similar results with respect to operating temperature, with both operating at ~255° C., significantly cooler and more uniform than the standard lamps in either of the mounting configurations tested.

Finite Element Analysis of Temperature and Stress Profiles

To verify the design changes made in the lamps configured as disclosed herein (for example, as illustrated in FIGS. 6 and 7) improved upon temperature and stress profiles as compared to standard UV lamps, Finite Element Analysis (FEA) was used to produce a thermal and stress model of the standard lamp and a lamp configured as disclosed herein. The FEA was informed by the in-house pinch temperature testing to ensure that the model was representative of the real-life results.

Figure 14A:
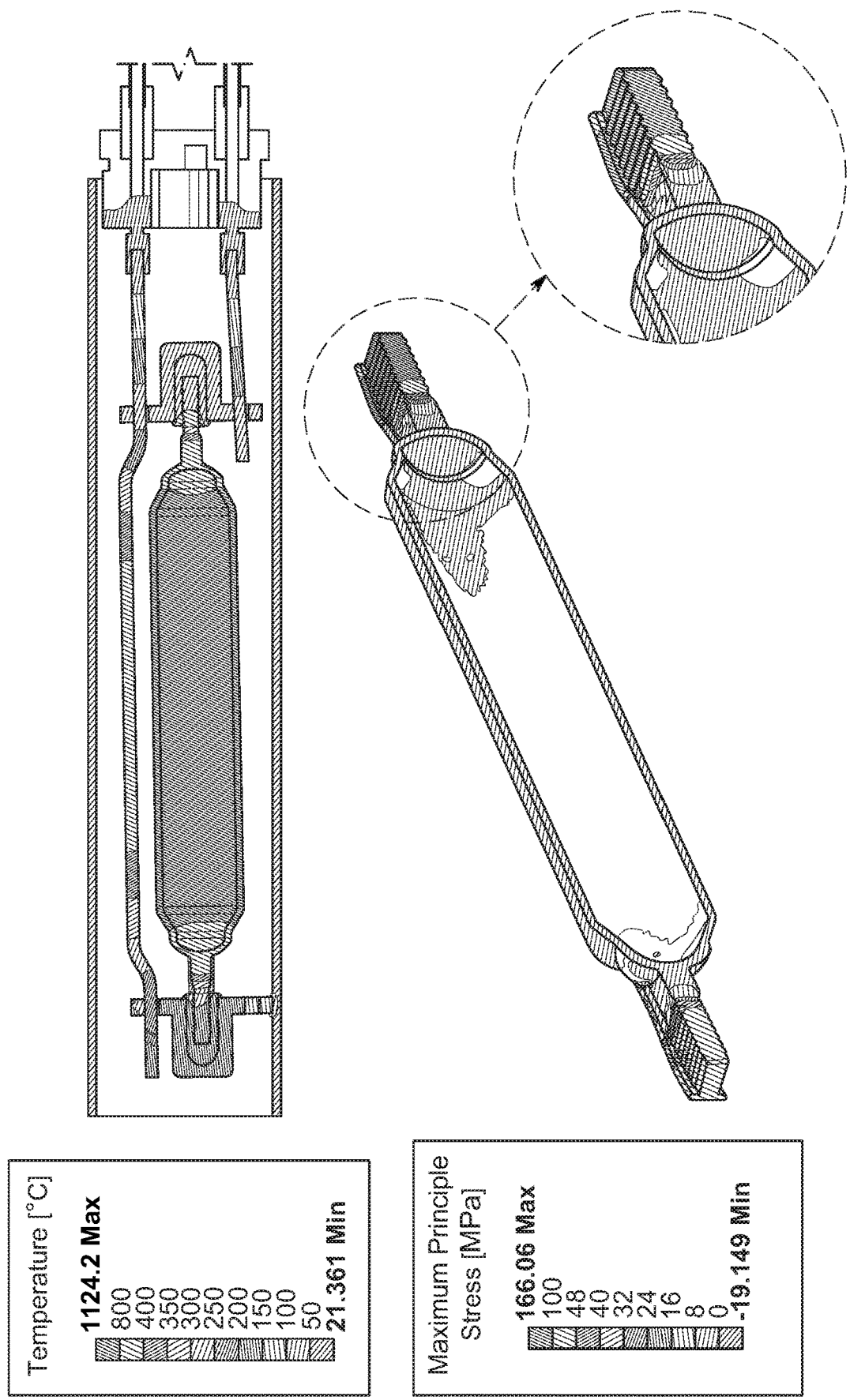
FIG. 14A illustrates the results of finite element analysis of temperature and stress distributions within a standard UV lamp.
Figure 14B:
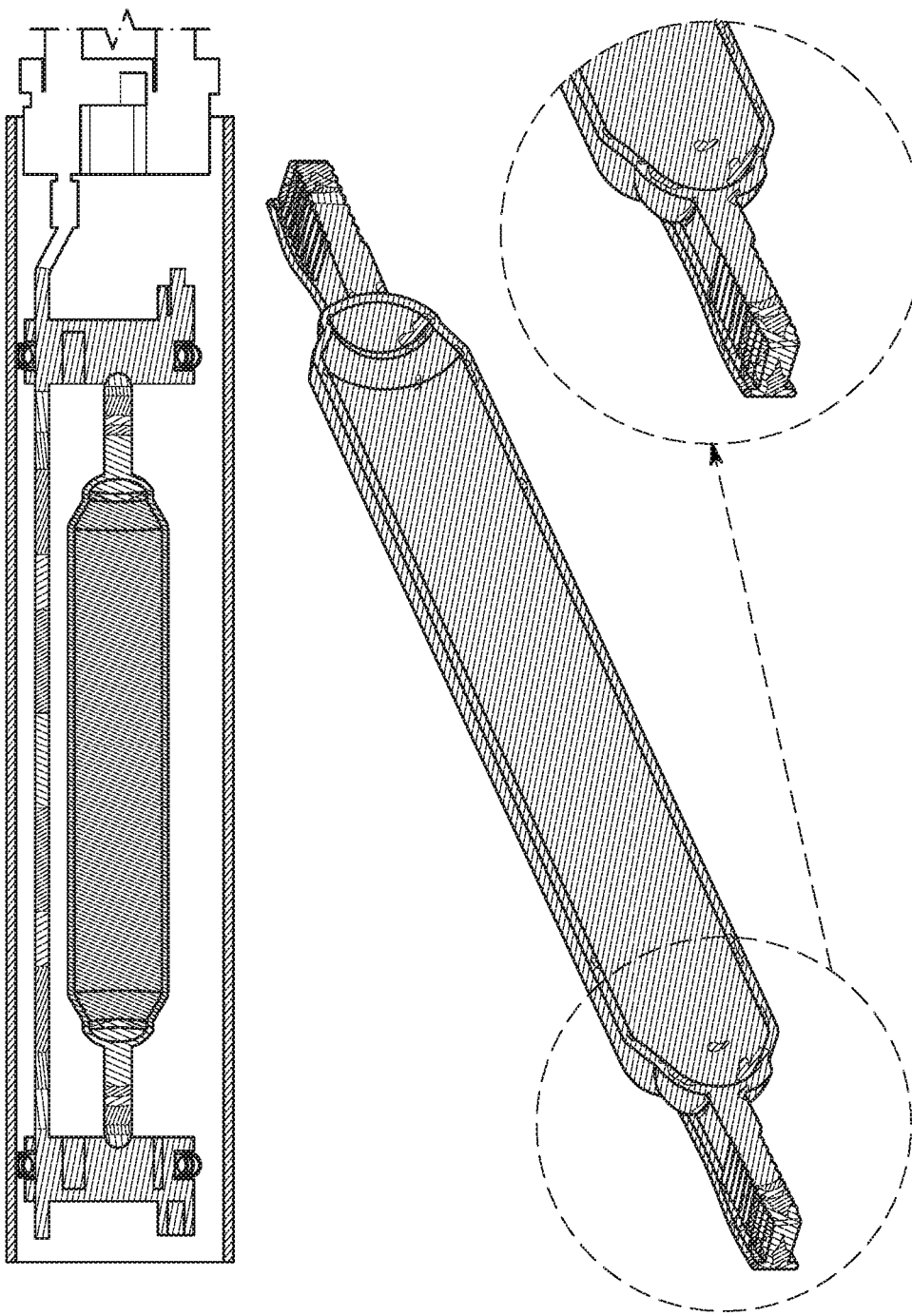
FIG. 14B illustrates the results of finite element analysis of temperature and stress distributions within a UV lamp as illustrated in FIG. 6.

FIG. 14A illustrates results of the FEA thermal and stress analysis for the standard lamp. FIG. 14B illustrates results of the FEA thermal and stress analysis for a lamp configured as disclosed herein. The thermal analysis matches the real-life data very closely, which shows that the model is accurate. The results of the thermal analysis show good reduction in temperature at the pinches of the lamp configured as disclosed herein, which again matches the real data. The stress analysis shows a high level of stress at the pinches of the standard lamp (especially at the near side, where the majority of failures are seen). Without being bound to a particular theory, this is believed to be caused by the expansion of the ceramic pulling the pinch. The stress seen significantly exceeds the tensile yield stress of the quartz of the pinches. The stress is greatly reduced in the lamp configured as disclosed herein and does not exceed tensile yield stress of the pinches. The heat and stress distribution of the lamp configured as disclosed herein is substantially symmetrical from one end of the lamp to the other, while the standard UV lamp exhibits substantially higher temperatures and stresses at one end as compared to the other.

Strike Cycle Testing

To perform a worst case/accelerated life test, two lamps as illustrated in FIGS. 6 and 7 were run for 20 mins on, 10 mins off, for 100 hours. This correlates to roughly 1 year of running (1 strike a day).

Before the test was started, the striking current, running current, and running voltage was found for each lamp. This was repeated at the end of the test, to understand any changes that had occurred. During testing the striking current was monitored. At the end of testing, the lamp parameters were still well within the characteristic tolerances, and both lamps were still running well.

After the test, the lamps were also visually inspected for any signs of wear/damage. Both lamps showed signs of black ends, presumably due to electrode sputtering (tungsten coating of the electrode is lost and condenses on the quartz sleeve). This is quite normal for lamps that have run a full lifetime, and is exacerbated by frequent strikes, which is how this test was run. The lamps otherwise looked in good condition, and none of the previous failure modes (e.g., pinch breakage) could be identified.

This testing indicates that the disclosed lamp design exhibits a high level of reliability.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Having thus described several aspects of at least one embodiment, it is to be appreciated various alterations, modifications, and improvements will readily occur to those skilled in the art. Any feature described in any embodiment may be included in or substituted for any feature of any other embodiment. Such alterations, modifications, and improvements are intended to be part of this disclosure, and are intended to be within the scope of the invention. Accordingly, the foregoing description and drawings are by way of example only.

What is claimed is:

1. A water treatment system comprising:
   an actinic radiation reactor; and
   at least one ultraviolet (UV) lamp disposed within a quartz tube within the actinic radiation reactor, the at least one UV lamp including:
   a lamp tube including a gas that emits ultraviolet light responsive to electrical excitation;
   a first pinch extending from a first end of the lamp tube and a second pinch extending from a second end of the lamp tube;
   a first end cap coupled to the first pinch and a second end cap coupled to the second pinch, the first end cap and second end cap dimensioned to center the lamp tube coaxially within the quartz tube, the first end cap and second end cap each including outer peripheral surfaces and slots extending inwardly from the outer peripheral surfaces; and
   an electrical conductor configured to provide power to the lamp tube disposed within the slots.

2. The system of claim 1, wherein the UV lamp further includes thermally conductive biasing elements disposed about respective peripheries of each of the first end cap and second end cap.

3. The system of claim 2, wherein the thermally conductive biasing elements comprise metallic springs.

4. The system of any one of claims 2-3, wherein the thermally conductive biasing elements are disposed within grooves defined within and circumscribing the outer peripheral surfaces of the first end cap and the second end cap.

5. The system of claim 4, wherein portions of the outer peripheral surfaces of the first end cap and second end cap are contoured to conform to an inner surface of the quartz tube.

6. The system of claim 4, wherein the slots are perpendicular to the grooves.

7. The system of claim 3, wherein the metallic springs retain the conductor within the slots.

8. The system of claim 2, wherein the thermally conductive biasing elements contact an inner surface of the quartz tube, support the lamp tube within the quartz tube, and dampen vibrations passing from the quartz tube to the first and second end caps.

9. The system of claim 1, wherein the lamp tube is configured to exhibit a symmetric temperature profile from the first pinch to the second pinch when in operation.

10. The system of claim 1, wherein the actinic radiation reactor is an ultraviolet advanced oxidation process reactor.

11. A method of treating water, the method comprising:
   introducing the water into an inlet of an actinic radiation reactor including at least one ultraviolet (UV) lamp disposed within a quartz tube within the actinic radiation reactor, the at least one UV lamp including:
   a lamp tube including a gas that emits ultraviolet light responsive to electrical excitation;
   a first pinch extending from a first end of the lamp tube and a second pinch extending from a second end of the lamp tube;
   a first end cap coupled to the first pinch and a second end cap coupled to the second pinch, the first end cap and second end cap dimensioned to center the lamp tube coaxially within the quartz tube, the first end cap and second end cap each including outer peripheral surfaces and slots extending inwardly from the outer peripheral surfaces; and an electrical conductor configured to provide power to the lamp tube disposed within the slots;

irradiating the water within the actinic radiation reactor with UV light from the at least one UV lamp to produce treated water; and withdrawing the treated water from the actinic radiation reactor.

12. A ultraviolet (UV) lamp configured to be disposed within a quartz tube within an actinic radiation reactor, the UV lamp comprising:

a lamp tube including a gas that emits ultraviolet light responsive to electrical excitation;

a first pinch extending from a first end of the lamp tube and a second pinch extending from a second end of the lamp tube;

a first end cap coupled to the first pinch and a second end cap coupled to the second pinch, the first end cap and second end cap dimensioned to center the lamp tube coaxially within the quartz tube, the first end cap and second end cap each including outer peripheral surfaces and slots extending inwardly from the outer peripheral surfaces;

an electrical conductor configured to provide power to the lamp tube disposed within the slots; and a means for vibrationally isolating at least one of the first end cap and the second end cap from the quartz tube disposed about respective peripheries of each of the first end cap and second end cap.

13. The UV lamp of claim 12, wherein the means for vibrationally isolating comprises thermally conductive elements.

14. The UV lamp of claim 13, wherein the thermally conductive elements comprise metallic springs.

15. The UV lamp of claim 14, wherein the metallic springs are disposed within grooves defined within and circumscribing the outer peripheral surfaces of the first end cap and the second end cap.

16. The UV lamp of claim 15, wherein portions of the outer peripheral surfaces of the first end cap and second end cap are contoured to conform to an inner surface of the quartz tube.

17. The UV lamp of claim 15, wherein the slots are perpendicular to the grooves.

18. The UV lamp of claim 15, wherein the metallic springs retain the electrical conductor within the slots.

19. The UV lamp of claim 13, wherein the thermally conductive elements contact an inner surface of the quartz tube, support the lamp tube within the quartz tube, and dampen vibrations passing from the quartz tube to the first and second end caps.

20. The UV lamp of claim 12, wherein, in operation, the lamp tube exhibits a symmetric temperature profile from the first pinch to the second pinch.

21. A method of retrofitting an actinic radiation reactor, the method comprising:

replacing at least one ultraviolet (UV) lamp within the actinic radiation reactor with a replacement lamp, the replacement lamp including:

a lamp tube including a gas that emits ultraviolet light responsive to electrical excitation;

a first pinch extending from a first end of the lamp tube and a second pinch extending from a second end of the lamp tube;

a first end cap coupled to the first pinch and a second end cap coupled to the second pinch, the first end cap and second end cap dimensioned to center the lamp tube coaxially within a quartz tube in the actinic radiation reactor, the first end cap and second end cap each including outer peripheral surfaces and slots extending inwardly from the outer peripheral surfaces; and an electrical conductor configured to provide power to the lamp tube disposed within the slots.

* * * * *